US008288474B2

(12) United States Patent
Hergenrother et al.

(10) Patent No.: US 8,288,474 B2
(45) Date of Patent: *Oct. 16, 2012

(54) COMPOUNDING SILICA-REINFORCED RUBBER WITH LOW VOLATILE ORGANIC COMPOUND (VOC) EMISSION

(75) Inventors: William L. Hergenrother, Akron, OH (US); Chenchy Jeffrey Lin, Hudson, OH (US); Terrence E. Hogan, Akron, OH (US); Ashley S. Hilton, Massillon, OH (US)

(73) Assignee: Bridgestone Corporation, Tokyo (JP)

( * ) Notice: Subject to any disclaimer, the term of this patent is extended or adjusted under 35 U.S.C. 154(b) by 50 days.

This patent is subject to a terminal disclaimer.

(21) Appl. No.: 12/883,778

(22) Filed: Sep. 16, 2010

(65) Prior Publication Data

US 2011/0180195 A1 Jul. 28, 2011

Related U.S. Application Data

(63) Continuation of application No. 11/387,569, filed on Mar. 23, 2006, now Pat. No. 7,799,870.

(60) Provisional application No. 60/664,757, filed on Mar. 24, 2005.

(51) Int. Cl.
*B60C 1/00* (2006.01)
*B32B 27/14* (2006.01)

(52) U.S. Cl. ........ 525/100; 428/403; 428/405; 524/424; 524/543; 524/571; 524/837; 528/17; 528/18; 528/21; 152/151

(58) Field of Classification Search .................. None
See application file for complete search history.

(56) References Cited

U.S. PATENT DOCUMENTS

| 2,462,640 | A |   | 2/1949  | Hyde |
|-----------|---|---|---------|------|
| 3,186,965 | A |   | 6/1965  | Plueddemanu |
| 3,304,318 | A |   | 2/1967  | Brady |
| 3,428,706 | A |   | 2/1969  | Walmsley et al. |
| 3,647,740 | A |   | 3/1972  | Loree et al. |
| 3,816,493 | A |   | 6/1974  | Nitzsche et al. |
| 4,101,460 | A |   | 7/1978  | Small et al. |
| 4,258,770 | A |   | 3/1981  | Davis et al. |
| 4,269,741 | A |   | 5/1981  | Homan |
| 4,340,515 | A |   | 7/1982  | Frassek et al. |
| 4,424,297 | A |   | 1/1984  | Bey |
| 4,512,897 | A |   | 4/1985  | Crowder, III et al. |
| 4,694,040 | A | * | 9/1987  | Hashimoto et al. ........... 524/765 |
| 4,745,145 | A |   | 5/1988  | Schofeld et al. |
| 4,822,681 | A |   | 4/1989  | Schossler et al. |
| 4,847,162 | A |   | 7/1989  | Haluska et al. |
| 4,889,747 | A |   | 12/1989 | Wilson |
| 5,015,717 | A |   | 5/1991  | Martin et al. |
| 5,162,409 | A |   | 11/1992 | Mroczkowski |
| 5,359,022 | A | * | 10/1994 | Mautner et al. ................ 528/23 |
| 5,363,994 | A |   | 11/1994 | Angeline |
| 5,447,971 | A |   | 9/1995  | Bergh et al. |
| 5,484,867 | A |   | 1/1996  | Lichtenhan et al. |
| 5,534,592 | A |   | 7/1996  | Halasa et al. |
| 5,552,476 | A |   | 9/1996  | Halling |
| 5,650,474 | A |   | 7/1997  | Yamaya et al. |
| 5,684,113 | A |   | 11/1997 | Nakanishi et al. |
| 5,750,197 | A |   | 5/1998  | van Ooij et al. |
| 5,750,610 | A |   | 5/1998  | Burns et al. |
| 5,763,388 | A |   | 6/1998  | Lightsey et al. |
| 5,830,934 | A |   | 11/1998 | Krishnan |
| 5,844,060 | A |   | 12/1998 | Furuya et al. |
| 5,854,369 | A |   | 12/1998 | Geck et al. |
| 5,907,015 | A |   | 5/1999  | Sexsmith |
| 5,914,364 | A |   | 6/1999  | Cohen et al. |
| 5,916,973 | A |   | 6/1999  | Zimmer et al. |
| 5,929,149 | A |   | 7/1999  | Matsuo et al. |
| 5,932,757 | A |   | 8/1999  | Standke et al. |
| 5,958,161 | A |   | 9/1999  | Grimberg et al. |
| 5,969,057 | A |   | 10/1999 | Schoeley et al. |
| 5,985,371 | A |   | 11/1999 | Fujioka et al. |
| 5,985,953 | A |   | 11/1999 | Lightsey et al. |
| 6,015,850 | A |   | 1/2000  | Nakamura et al. |
| 6,033,597 | A |   | 3/2000  | Yatsuyanagi et al. |
| 6,048,910 | A | * | 4/2000  | Furuya et al. .................. 522/86 |
| 6,124,491 | A |   | 9/2000  | Wolter et al. |
| 6,127,468 | A |   | 10/2000 | Cruse et al. |
| 6,140,447 | A |   | 10/2000 | Gay et al. |
| 6,162,547 | A |   | 12/2000 | van Ooji et al. |

(Continued)

FOREIGN PATENT DOCUMENTS

JP          11343366         12/1999

(Continued)

OTHER PUBLICATIONS

Peng, KuoLiang, May 11, 2011 Office Action from U.S. Appl. No. 12/347,047 (8 pp.).
Xue, Haijiao, May 19, 2011 Office Action with English translation from Chinese Patent Application No. 200680018058.2 (9 pp.).
Salvitti, Michael A., May 26, 2011 Office Action from U.S. Appl. No. 12/344,804 (11 pp.).
Peng, KuoLiang, Jun. 16, 2011 Office Action from U.S. Appl. No. 12/346,994 (10 pp.).
Journal of Applied Polymer Science, Reduction of Volatile Organic Compound Emission. I. Synthesis and Characterization of Alkoxy-Modified Silesquioxane vol. 115, 79-90 (2010) 2009 Wiley Periodicals, Inc.

(Continued)

*Primary Examiner* — Marc Zimmer
(74) *Attorney, Agent, or Firm* — Meredith E. Hooker; Nathan T. Lewis

(57) ABSTRACT

Alkoxy-modified silsesquioxane compounds are described. The alkoxy-modified silsesquioxane compounds contain an alkoxysilane group that participates in an alkoxysilane-silica reaction as a silica dispersing agent in rubber, with the release of zero to about 0.1% by weight of the rubber of volatile organic compounds (VOC), especially alcohol, during compounding and further processing. Further described are methods for making alkoxy-modified silsesquioxanes, methods for making vulcanizable rubber compounds containing alkoxy-modified silsesquioxanes, vulcanizable rubber compounds containing alkoxy-modified silsesquioxanes, and pneumatic tires comprising a component that contains alkoxy-modified silsesquioxanes.

92 Claims, 2 Drawing Sheets

U.S. PATENT DOCUMENTS

| | | |
|---|---|---|
| 6,191,247 B1 | 2/2001 | Ishikawa et al. |
| 6,204,339 B1 | 3/2001 | Waldman et al. |
| 6,232,424 B1 | 5/2001 | Zhong et al. |
| 6,239,243 B1 | 5/2001 | Deng et al. |
| 6,271,331 B1 | 8/2001 | Gay et al. |
| 6,294,007 B1 | 9/2001 | Martin |
| 6,313,205 B1 | 11/2001 | Chiron et al. |
| 6,326,424 B1 | 12/2001 | Louis et al. |
| 6,331,605 B1 | 12/2001 | Lunginsland et al. |
| 6,361,871 B1 * | 3/2002 | Jenkner et al. ........ 428/447 |
| 6,372,843 B1 | 4/2002 | Barruel et al. |
| 6,399,210 B1 | 6/2002 | Zhong |
| 6,414,061 B1 | 7/2002 | Cruse et al. |
| 6,426,378 B1 | 7/2002 | Lickes et al. |
| 6,429,245 B1 | 8/2002 | Francik et al. |
| 6,433,065 B1 | 8/2002 | Lin et al. |
| 6,433,077 B1 | 8/2002 | Craig et al. |
| 6,455,158 B1 | 9/2002 | Mei et al. |
| 6,465,670 B2 | 10/2002 | Thise et al. |
| 6,465,671 B1 | 10/2002 | Bae et al. |
| 6,528,673 B2 | 3/2003 | Cruse et al. |
| 6,548,573 B1 | 4/2003 | Rempert |
| 6,548,594 B2 | 4/2003 | Luginsland et al. |
| 6,573,356 B2 | 6/2003 | Araki et al. |
| 6,608,125 B2 | 8/2003 | Cruse et al. |
| 6,611,518 B1 | 8/2003 | Ngo et al. |
| 6,624,214 B2 | 9/2003 | Zimmer et al. |
| 6,624,237 B2 | 9/2003 | Biteau et al. |
| 6,635,700 B2 | 10/2003 | Cruse et al. |
| 6,649,684 B1 | 11/2003 | Okel |
| 6,653,365 B2 | 11/2003 | Jia |
| 6,660,823 B1 | 12/2003 | Lichtenhan et al. |
| 6,683,135 B2 | 1/2004 | Cruse et al. |
| 6,689,834 B2 | 2/2004 | Ackermann et al. |
| 6,696,155 B1 | 2/2004 | Takano et al. |
| 6,727,339 B2 | 4/2004 | Luginsland et al. |
| 6,767,930 B1 | 7/2004 | Svejda et al. |
| 6,770,724 B1 | 8/2004 | Lichtenhan et al. |
| 6,774,202 B2 | 8/2004 | Lee |
| 6,774,569 B2 | 8/2004 | de Vries et al. |
| 6,811,684 B2 | 11/2004 | Mohr et al. |
| 6,841,197 B2 | 1/2005 | Standke et al. |
| 6,852,794 B2 | 2/2005 | Puhala et al. |
| 6,878,768 B2 | 4/2005 | Tardivat et al. |
| 6,890,981 B1 | 5/2005 | Luginsland |
| 6,903,150 B2 | 6/2005 | Zimmer et al. |
| 6,911,518 B2 | 6/2005 | Lichtenhan et al. |
| 6,919,469 B2 | 7/2005 | Van Ooij et al. |
| 6,927,270 B2 | 8/2005 | Lichtenhan et al. |
| 6,972,312 B1 | 12/2005 | Lichtenhan et al. |
| 7,119,150 B2 | 10/2006 | Lin et al. |
| 7,201,944 B2 | 4/2007 | Hergenrother et al. |
| 7,393,564 B2 | 7/2008 | Hergenrother et al. |
| 7,432,321 B2 | 10/2008 | Joshi et al. |
| 7,732,016 B2 | 6/2010 | van Ooij et al. |
| 7,799,870 B2 | 9/2010 | Hergenrother et al. |
| 7,915,368 B2 | 3/2011 | Hergenrother et al. |
| 8,097,674 B2 | 1/2012 | Hergenrother et al. |
| 2001/0011046 A1 | 8/2001 | Ichikawa et al. |
| 2002/0055564 A1 | 5/2002 | Cruse et al. |
| 2002/0061409 A1 | 5/2002 | Topp et al. |
| 2003/0055193 A1 | 3/2003 | Lichtenhan et al. |
| 2003/0059393 A1 | 3/2003 | Wrolson et al. |
| 2003/0088034 A1 | 5/2003 | Luginsland et al. |
| 2003/0130388 A1 | 7/2003 | Luginsland et al. |
| 2003/0199619 A1 * | 10/2003 | Cruse ........ 524/261 |
| 2004/0042880 A1 * | 3/2004 | Lee ........ 414/277 |
| 2004/0042980 A1 | 3/2004 | Kanji et al. |
| 2004/0122180 A1 | 6/2004 | Hergenrother et al. |
| 2004/0210001 A1 | 10/2004 | Cruse et al. |
| 2004/0266968 A1 | 12/2004 | Korth et al. |
| 2005/0009982 A1 | 1/2005 | Inagaki et al. |
| 2005/0010012 A1 | 1/2005 | Jost et al. |
| 2005/0244659 A1 | 11/2005 | Higuchi et al. |
| 2005/0277717 A1 | 12/2005 | Joshi et al. |
| 2006/0083925 A1 | 4/2006 | Laine et al. |
| 2006/0086450 A1 | 4/2006 | Hogan et al. |
| 2006/0089446 A1 | 4/2006 | Lin et al. |
| 2006/0089504 A1 * | 4/2006 | Ito et al. ........ 556/407 |
| 2006/0217473 A1 | 9/2006 | Hergenrother et al. |
| 2007/0059448 A1 | 3/2007 | Smith et al. |
| 2007/0275255 A1 | 11/2007 | Ooms et al. |
| 2008/0293858 A1 | 11/2008 | Hergenrother et al. |
| 2009/0165913 A1 | 7/2009 | Hergenrother et al. |
| 2009/0171014 A1 | 7/2009 | Hergenrother et al. |
| 2009/0181248 A1 | 7/2009 | van Ooij et al. |
| 2009/0326255 A1 | 12/2009 | Hergenrother et al. |
| 2010/0071818 A1 | 3/2010 | Hergenrother et al. |

FOREIGN PATENT DOCUMENTS

| | | |
|---|---|---|
| JP | 2002-138164 | 5/2002 |
| WO | 2005-093002 | 10/2005 |
| WO | 2006-031434 | 3/2006 |
| WO | 2008-025846 | 3/2008 |
| WO | 2009-085181 | 7/2009 |

OTHER PUBLICATIONS

Brown, Jr., John F. et al., "The Polycondensation of Phyenlsilanetriol", Journal of the American Chemical Society, vol. 87, No. 19, pp. 4317-4324 (Oct. 5, 1965).

Dittmar, Uwe et al., "Funktionalisierte Octa-(propylsilsesquioxane)(3-XC$_3$H$_6$)$_8$(Si$_8$O$_{12}$) Modellverbindungen fur oberflachenmodifizierte Kieselgele", Journal of Organometallic Chemistry, 489 pp. 185-194, (1995) [with English translation].

Dzhafarov, A.A. et al., "Synthesis and Properties of Organosilicon, Organogermanium, and Organotin Compounds [2-(Arylthio)Ethyl]-Silanes, -Germanes, and -Stannanes", Kalinin State University, Institute of Oil-Additive Chemistry, Academy of Sciences of the Azerbaidzhan SSR. Translated from Zhurnal Obshchei Khimii, vol. 45, No. 9, pp. 2023-2025, Sep. 1975.

Joshi, Mangala et al., "Polymeric Nanocomposites—Polyhedral Oligomeric Silsesquioxanes (POSS) as Hybrid Nanofiller", Journal of Macromolecular Science, Part C—Polymer Reviews, vol. 44, No. 4, pp. 389-410 (2004).

Nuss, A.J. et al., Decision of Technical Board of Appeal 3.3.1 dated Feb. 12, 1998, T990/96-3.3.1 (pp. 1-12).

Rikowski, Eckhard et al., "Cage-rearrangement of silsesquioxanes", Polyhedron, vol. 16, No. 19, pp. 3357-3361 (1997).

Van Ooij, W.J., "Mechanism and Theories of Rubber Adhesion to Steel Tire Cords", Rubber Chemistry and Technology, vol. 57, No. 3, pp. 421-456 (1984).

Yu, Libing et al., "Preparation, Characterization, and Synthetic Uses of Lanthanide (III) Catalysts Supported on Ion Exchange Resins", J. Org. Chem., vol. 62, No. 11, pp. 3575-3581 (1997).

Product brochure, Gelest, Inc., "PolySilsesquioxanes and T-Resins RSiO$_{1.5}$", pp. 39-42, (2004).

Boiling Point Calculator from the web site http://www.partyman.se/boiling-point-calculator, downloaded Nov. 10, 2009 (2pp.).

Boiling Point Calculator from the web site http://www.trimen.pl/witek/calculators/wrzenie.html, downloaded Nov. 10, 2009 (2 pp.).

Database WPI Week 200026, Thomson Scientific, London, GB; AN 2000-298587, XP-002573380, & JP2000-086766, Mar. 28, 2000 (2 pp.).

Buestrich, R., Jul. 24, 2006 International Search Report from PCT Patent Application No. PCT/US2006/010610 (2 pp.).

Buestrich, Ralf, Apr. 15, 2008 Office Action from corresponding European Patent Application No. 06739416.3 (3 pp.).

Zimmer, Marc S., Jun. 26, 2009 Office Action from U.S. Appl. No. 11/387,569 (6 pp.).

Buestrich, Ralf, Aug. 17, 2009 Office Action from corresponding European Patent Application No. 06739416.3 (4 pp.).

Zimmer, Marc S., Nov. 20, 2009 Final Office Action from U.S. Appl. No. 11/387,569 (6 pp.).

Nazina, Elena E., Mar. 22, 2010 Office Action from corresponding Russian Patent Application No. 2007139319 (6 pp.).

Cho, Han Sol, Apr. 20, 2010 International Search Report from PCT/US2009/069587 (4 pp.).

Xue, Haijiao, English translation of Apr. 27, 2010 First Office Action from corresponding Chinese Patent Application No. 200680018058.2 (11 pp.).

Salvitti, Michael A., Apr. 29, 2010 Office Action from corresponding U.S. Appl. No. 12/344,804 (11 pp.).
Peng, Kuo Liang, May 18, 2010 Office Action from corresponding U.S. Appl. No. 11/752,715 (7 pp.).
Salvitti, Michael A., Sep. 2, 2010 Final Office Action from corresponding U.S. Appl. No. 12/344,804 (14 pp.).
Zimmer, Marc S., Oct. 5, 2010 Office Action from corresponding U.S. Appl. No. 12/347,017 (10 pp.).
Peng, Kuo Liang, Nov. 18, 2010 Notice of Allowance from corresponding U.S. Appl. No. 11/752,715 (5 pp.).
Salvitti, Michael A., Dec. 27, 2010 Advisory Action from corresponding U.S. Appl. No. 12/344,804 (7 pp.).
Zimmer, Marc S., Apr. 21, 2011 Notice of Allowance from corresponding U.S. Appl. No. 12/347,017 (5 pp.).
Hergenrother, William L. et al., U.S. Appl. No. 12/344,804, filed Dec. 29, 2008 entitled "Methods of Making Blocked-Mercapto Alkoxy-Modified Silsesquioxane Compounds".
Hergenrother, William L. et al., U.S. Appl. No. 12/346,994, filed Dec. 31, 2008 entitled "Amino Alkoxy-Modified Silsesquioxanes and Method of Preparation".
Hergenrother, William L. et al., U.S. Appl. No. 12/347,017, filed Dec. 31, 2008 entitled "Amino Alkoxy-Modified Silsesquioxanes in Silica-Filled Rubber With Low Volatile Organic Chemical Evolution".
Hergenrother, William L. et al., U.S. Appl. No. 12/347,047, filed Dec. 31, 2008 entitled "Method for Making Alkoxy-Modified Silsesquioxanes and Amino Alkoxy-Modified Silsesquioxanes".
Hergenrother, William L. et al., U.S. Appl. No. 12/347,086, filed Dec. 31, 2008 entitled "Amino Alkoxy-Modified Silsesquioxane Adhesives for Improved Metal Adhesion and Metal Adhesion Retention to Cured Rubber".

Baney, Ronald H. et al., "Silsesquioxanes," Chem. Rev. vol. 95, pp. 1409-1430 (1995).
Li, Guizhi et al., "Polyhedral Oligomeric Silsesquioxane (POSS) Polymers and Copolymers: A Review," Journal of Inorganic and Organometallic Polymers, vol. 11, No. 3, pp. 123-154 (2002).
Peng, Kuo Liang, Nov. 17, 2011 Final Office Action from U.S. Appl. No. 12/347,047 (10 pp.).
Peng, Kuo Liang, Nov. 18, 2011 Final Office Action from U.S. Appl. No. 12/346,994 (10 pp.).
Salvitti, Michael A., Nov. 25, 2011 Final Office Action from U.S. Appl. No. 12/344,804 (15 pp.).
Sheh, Anthony H., Feb. 6, 2012 Office Action from U.S. Appl. No. 12/347,086 (12 pp.).
Kamimura, N., English translation of Feb. 7, 2012 Office Action from Japanese Patent Application No. 2008-503194 (7 pp.).
Peng, Kuo Liang, Mar. 1, 2012 Office Action from U.S. Appl. No. 12/347,047 (7 pp.).
Peng, Kuo Liang, Mar. 2, 2012 Office Action from U.S. Appl. No. 12/346,994 (8 pp.).
Peng, Kuo Liang, Mar. 22, 2012 Office Action from U.S. Appl. No. 13/030,611 (7 pp.).
Salvitti, Michael A., Apr. 6, 2012 Advisory Action from U.S. Appl. No. 12/344,804 (8 pp.).
Buestrich, Ralf, Apr. 23, 2012 Office Action from European Patent Application No. 10075613.9 (6 pp.).
Buestrich, Ralf, Apr. 24, 2012 Office Action from European Patent Application No. 06739416.3 (6 pp.).

* cited by examiner

COMPOUNDING SILICA-REINFORCED RUBBER WITH LOW VOLATILE ORGANIC COMPOUND (VOC) EMISSION

CROSS-REFERENCE TO RELATED APPLICATION

This application is a continuation of U.S. application Ser. No. 11/387,569, which was filed on Mar. 23, 2006, now U.S. Pat. No. 7,799,870 which in turn claimed priority to provisional application 60/664,757 filed Mar. 24, 2005.

FIELD OF THE INVENTION

This technology generally relates to alkoxy-modified silsesquioxane compounds and the use of such compounds as dispersing agents in vulcanizable elastomeric compounds containing silica as a reinforcing filler.

BACKGROUND OF THE INVENTION

When producing elastomeric compositions for use in rubber articles, such as tires, power belts, and the like, it is desirable that these elastomeric compositions are easily processable during compounding and have a high molecular weight with a controlled molecular weight distribution, glass transition temperature ($T_g$) and vinyl content. It is also desirable that reinforcing fillers, such as silica and/or carbon black, be well dispersed throughout the rubber in order to improve various physical properties, such as the compound Mooney viscosity, modulus, tangent delta (tan δ), and the like. Rubber articles, especially tires, produced from vulcanized elastomers exhibiting these improved properties will have reduced hysteresis, better rolling resistance, snow and ice traction, wet traction, and improved fuel economy for vehicles equipped with such tires.

Mixing silica into rubber stocks, however, is difficult because silica particles containing polar silanol groups on the surface, tend to self-associate and reagglomerate extensively after compounding, leading to poor silica dispersion and a high compound viscosity. The strong silica filler network results in a rigid uncured compound that is difficult to process in extrusion and forming operations.

To alleviate this problem, various silica coupling agents including, but not limited to, the well known bis(trialkoxysilylorgano) polysulfides (e.g., tetrasulfides and disulfides) and combinations of octyltriethoxysilane and mercaptoalkyltrialkoxysilanes have been employed to improve silica dispersion and compound viscosity. These coupling agents have a moiety (e.g., an alkoxysilyl group) that is reactive with the silica surface and a moiety (e.g., a mercapto or another sulfur group) that binds to the polymer.

Organoalkoxysilane compounds have also been employed as agents that react with the silica surface as shielding or hydrophobtaining agents to improve dispersion and compound viscosity. The alkoxysilyl groups of these compounds react with the silica surface but do not have a moiety that binds to the polymer. Well-known examples of these agents include, but are not limited to, alkyltrialkoxysilanes such as octyltriethoxysilanes, decyltriethoxysilanes, dodecyltriethoxysilanes, and their trimethoxysilane counterparts, and the like. In addition, it is known to terminate elastomers with a functional group that contains a silica-reactive alkoxysilane group to improve compound properties.

A feature of all of the aforementioned silica dispersing agents and functionalized elastomers is the presence of one or more alkoxysilane groups that react with the silanol groups on the silica surface (the alkoxysilane-silica reaction) during mixing of the rubber compound, with the evolution and release of alcohol into the environment. In particular, when the mixing is conducted at high processing temperatures, alcohol is released and contributes to the volatile organic compounds (VOCs) generated and potentially released during processing of the rubber compounds. At lower processing temperatures, the compounded product can retain a considerable amount of unreacted alkoxysilyl groups that are available to further react with the silica and moisture during storage, extrusion, tire build, and/or curing, resulting in an undesirable increase in the compound viscosity, and a shorter shelf life. This continuing reaction in the compounded product evolves additional alcohol which may impair further processing of the compound. As a result, a low tread strip drawing speed must be maintained to ensure the drawn product conforms to specifications, resulting in a decrease in production and a concomitant increase in costs.

As the present trend in rubber-making technology continues toward the use of higher silica loadings in rubber compounds, there is a challenge to contain levels of environmentally released alcohol. In addition, there is a need to reduce the amount of alcohol retained in the compounded product, in order to increase production and decrease costs. Therefore, a need exists to significantly reduce or eliminate the evolution of alcohol during compounding, processing, cure and storage of silica-reinforced rubbers.

SUMMARY

Alkoxy-modified silsesquioxane compounds are described herein. The alkoxy-modified silsesquioxane compounds comprise an alkoxysilane group that participates in an alkoxysilane-silica reaction as a silica dispersing agent in rubber, with the release of zero to about 0.1% by weight of the rubber of volatile organic compounds (VOC), especially alcohol, during compounding and further processing. Further described are methods for making alkoxy-modified silsesquioxanes, methods for making vulcanizable rubber compounds containing alkoxy-modified silsesquioxanes, vulcanizable rubber compounds containing alkoxy-modified silsesquioxanes, and pneumatic tires comprising a component that contains alkoxy-modified silsesquioxanes.

In particular, the alkoxy-modified silsesquioxanes described are selected from the group consisting of alkoxy-modified silsesquioxanes having the formula

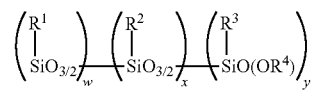

and mixtures thereof, wherein w, x and y represent mole fractions, y does not equal zero, either w or x, but not both, can be zero, and w+x+y=1.00, wherein $R^1$, $R^2$ and $R^3$ are the same or different and selected from the group consisting of (i) H or an alkyl groups having one to about 20 carbon atoms, (ii) cycloalkyl groups having 3 to about 20 carbon atoms, (iii) alkylaryl groups having 7 to about 20 carbon atoms, and (iv) $R^5X$, wherein X is selected from the group consisting of Cl, Br, SH, $S_aR^6$, $NR^6_2$, $OR^6$, $CO_2H$, $SCOR^6$, $CO_2R^6$, OH, olefins, epoxides, amino groups, vinyl groups, acrylates and methacrylates, wherein a=1 to about 8, $R^5$ is selected from the group consisting of alkylene groups having one to about 20 carbon atoms, cycloalkylene groups having 3 to about 20 carbon atoms, and $R^4$ and $R^6$ are selected from the group consisting of alkyl groups having one to about 5 carbon atoms, cycloalkyl groups having 3 to about 20 carbon atoms, and alkylaryl groups having 7 to about 20 carbon atoms.

Vulcanized rubber compounds containing the alkoxy-modified silsesquioxanes have enhanced rubber reinforcement, increased polymer-filler interaction and lower compound viscosity, providing for tires having improved wet and snow traction, lower rolling resistance, increased rebound and decreased hysteresis.

DETAILED DESCRIPTION OF THE INVENTION

Figure 1:
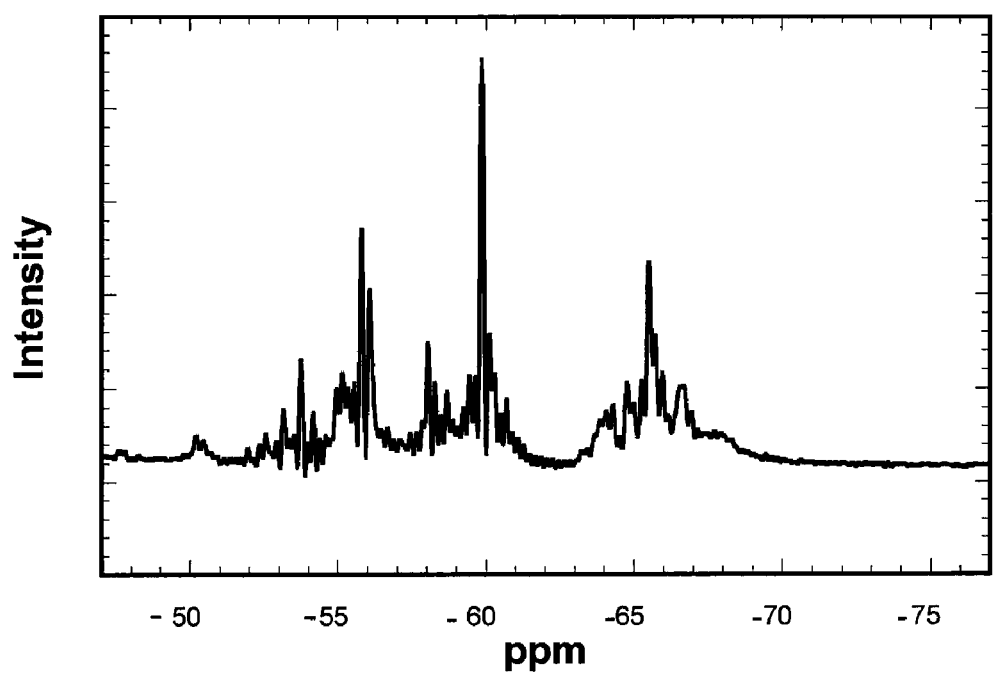
FIG. 1 illustrates a nuclear magnetic resonance (NMR) analysis of the $^{29}$Si content of a pure closed caged POSS structure that shows a definitive peak at about −68 (parts per million (ppm)). The illustrated POSS structure is a mixture of closed polyhedral $Si_8O_{12}$ ($T_8$), $Si_{10}O_{15}$ ($T_{10}$) and $Si_{12}O_{18}$ ($T_{12}$) structures. This structure is prior art and is not illustrative of the alkoxy-modified silsesquioxanes according to the present invention.

The alkoxy-modified silsesquioxane (AMS or co-AMS) compound or compounds of the invention have the following formula

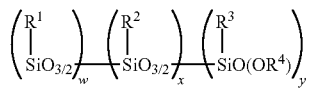

and mixtures thereof, wherein w, x and y represent mole fractions, y does not equal zero, either w or x, but not both, can be zero, and w+x+y=1.00, wherein $R^1$, $R^2$ and $R^3$ are the same or different and selected from the group consisting of (i) H or an alkyl groups having one to about 20 carbon atoms, (ii) cycloalkyl groups having 3 to about 20 carbon atoms, (iii) alkylaryl groups having 7 to about 20 carbon atoms, and (iv) $R^5X$, wherein X is selected from the group consisting of Cl, Br, SH, $S_aR^6$, $NR^6_2$, $OR^6$, $CO_2H$, $SCOR^6$, $CO_2R^6$, OH, olefins, epoxides, amino groups, vinyl groups, acrylates and methacrylates, wherein a=1 to about 8, $R^5$ is selected from the group consisting of alkylene groups having one to about 20 carbon atoms, cycloalkylene groups having 3 to about 20 carbon atoms, and $R^4$ and $R^6$ are selected from the group consisting of alkyl groups having one to about 5 carbon atoms, cycloalkyl groups having 3 to about 20 carbon atoms, and alkylaryl groups having 7 to about 20 carbon atoms.

In general, the AMS compound(s) can be made by subjecting an alkyltrialkoxysilane or an alkyltrichlorosilane to hydrolysis and condensation in an aqueous alcohol solution in the presence of a condensation catalyst. The reaction is continued for a period of time sufficient for substantially total conversion of the alkyltrialkoxysilane or alkyltrichlorosilane to the AMS compound(s). It has been found that controlling the amounts of water in the reaction mixture can speed the conversion of the reactants to the final product. The AMS product is then removed from the reaction mixture by phase separation, and any remaining AMS product in the reaction mixture can be extracted with water and an organic solvent such as, but not limited to, cyclohexane and the like. The AMS product can then be dried in a warm vacuum oven, to remove substantially any alcohol and water remaining in the reaction mixture. The resulting product is a liquid or solid, preferably a highly viscous liquid, substantially free of moisture and of free alcohol.

A suitable method for preparing the AMS compound(s) is described in the examples below. And from the teachings of this disclosure, other methods for making the compound(s) will become apparent to those skilled in the art.

Suitable hydrolysis and condensation catalysts for use in making the AMS compounds are known and include, but are not limited to, strong acids such as hydrochloric acid, sulfuric acid, phosphoric acid and the like, strong bases such as sodium hydroxide, potassium hydroxide, lithium hydroxide and the like, and strong organic acids and bases, such as (1,8-diazabicyclo [5.4.0] undec-7-ene), imidazoles, guanidines and the like, known to those skilled in the art. Strong acid catalysts are particularly suitable for use in making the AMS compounds. The amount of the catalyst used is based upon the desired effective rate of the reaction. It will be recognized that when an alkyltrichlorosilane is used as the reactant, the addition of water to the reaction mixture will result in the production of hydrochloric acid, so no further catalyst is necessary to the reaction.

The temperature at which the reaction takes place is not critical. For example, almost identical yields of AMS product can be obtained from ambient temperature (about 25° C.) to about 60° C. to about 100° C. The AMS product can be observed as a cloudy residue that, if desired, can be progressively removed from the reaction mixture over a period of time until there is substantially total conversion of the reactants to the AMS product. Moreover, during the reaction, additional amounts of the alkyltrialkoxysilane or alkyltrichlorosilane reactants can be added, with water, to continuously yield product.

The period of time for total conversion of the reactants to the AMS product depends on the original concentration of the reactants and the optional addition of reactants and/or applied heat during the process. However, if no additional reactants are used, the time can range from about 0.5 hours to about 200 hours, often about 0.75 hours to about 120 hours, or about one hour to about 72 hours. The time for total conversion is defined as the time elapsed until no further product can be removed by phase separation and no further product can be extracted from the reaction mixture by water and organic solvent, as described above.

Exemplary alkyltrialkoxysilane reactants in making the AMS products can include, but are not limited to, octyltriethoxysilane, octyltrimethoxysilane, cyclohexyltriethoxysilane, isobutyltriethoxysilane, ethyltrimethoxysilane, cyclohexyltributoxysilane, methyl-triethoxysilane, propyltriethoxysilane, hexyltriethoxysilane, heptyltriethoxysilane, nonyl-triethoxysilane, decyltriethoxysilane, n-dodecyltrialkoxysilane, octadecyltriethoxysilane, methyltrimethoxysilane, propyltrimethoxysilane, hexyltrimethoxysilane, heptyl-trimethoxysilane, nonyltrimethoxysilane, octadecyl-trimethoxysilane, 2-ethylhexyl-triethoxysilane, and the like, and mixtures thereof.

Exemplary alkyltrichlorosilane reactants for making the AMS compounds can include, but are not limited to, octyltrichlorosilane, cyclohexyltrichlorosilane, isobutyltrichlorosilane, ethyltrichlorosilane, methyltrichlorosilane, propyltrichlorosilane, hexyltrichlorosilane, heptyltrichlorosilane, nonyltrichlorosilane, octadecyltrichlorosilane, and the like, and mixtures thereof.

Co-AMS compounds can be obtained by co-reacting any alkyltrialkoxysilane or alkyltrichlorosilane by hydrolysis and condensation with another compound that can provide a functional group ($XR^5$, as defined above) on the AMS compound. For example, for use in rubber compounds, it may be desirable to produce a co-AMS compound containing a sulfur atom that can bind to an elastomer. Therefore, a suitable co-AMS compound can be manufactured by the co-hydrolysis and co-condensation of an alkyltrialkoxysilane or an alkyltrichlorosilane with, for example, a mercaptoalkyltrialkoxysilane to introduce a mercaptoalkyl functionality, or with a blocked mercaptoalkyltrialkoxysilane to introduce a blocked mercaptoalkyl functionality.

In this description the use of the term "blocked mercaptoalkyltrialkoxysilane" is defined as a mercaptosilane silica coupling agent that comprises a blocking moiety that blocks the mercapto part of the molecule (i.e. the mercapto hydrogen atom is replaced by another group, hereafter referred to as "blocking group") while not affecting the silica-reactive mercaptosilane moiety. Suitable blocked mercaptosilanes can include, but are not limited to, those described in U.S. Pat. Nos. 6,127,468; 6,204,339; 6,528,673; 6,635,700; 6,649,684; 6,683,135; the disclosures of which are hereby incorporated by reference with respect to the examples described. For purposes of this disclosure, the silica-reactive "mercaptosilane moiety" is defined as the molecular weight equivalent to the molecular weight of γ-mercaptopropyl triethoxysilane. A deblocking agent can be added later in the manufacturing process, after the silica-silane reaction has occurred, to allow the sulfur atom of the mercaptosilane to bond rapidly with the rubber. The deblocking agent can be added at any time during the compounding process as a single component during any mixing stage in which deblocking is desired. Often deblocking is desired during the curing stage of compounding and the addition of the deblocking agent is added in the final mixing stage. The deblocking agent can be contained in a sulfur cure package and, often, can function as a cure accelerator, especially in combination with a zinc salt. Examples of deblocking agents are well known to those skilled in the art.

The resulting AMS or co-AMS products are usually a mixture of oligomers of all sizes, from which one or more compounds of specific size or molecular weight can be separated from the mixture by known methods, such as chromatography and the like. Suitably, these one or more products are alkoxy-modified silsesquioxanes. For example, such alkoxy-modified silsesquioxanes can include, but are not limited to, octyl alkoxy-modified silsesquioxanes, phenyl alkoxy-modified silsesquioxanes, 3-chloropropyl alkoxy-modified silsesquioxanes, 3-mercaptopropyl alkoxy-modified silsesquioxanes, thioacylpropyl alkoxy-modified silsesquioxanes, and the like, and mixtures of any of these. Suitably, the alkoxy-modified silsesquioxane can comprise an alkyl-co-mercapto alkoxy-modified silsesquioxane.

A feature of each of the AMS or co-AMS products produced is the presence of a reactive alkoxysilyl group "y" attached to one or more alkoxy-modified silsesquioxane "w" and/or "x" groups. In an AMS compound, either w or x but not both can be zero. In a co-AMS, w and x are not zero. The mole fraction of the one or more w or x groups is calculated as the mole fraction of w or x divided by the sum of the mole fractions w+x. Suitably, ratios of the w mole fraction (or the ratio of the x mole fraction) to the sum of the w+x fraction can range from about 0.01 to about 0.5. The mole fractions of x, y and z also can be measured through the mole fractions of $R^1$, $R^2$, and $R^3$ if the relative abundance of those groups can be measured. The sum of the mole fractions w, x and y is always equal to one, and y is never zero.

The individual weight fractions of w, x and y can be calculated from the mole fraction of each times their respective formula weight (FW) divided by the sum of the individual w, x and y weight fractions. For example, the weight percent of x (W % (x)) is calculated as $$W \%(x) = \frac{x(FW_x)}{x(FW_x) + w(FW_w) + y(FW_y)} \times 100$$

The weight percent of alcohol ($HOR^4$) can be calculated by the formula $$W \%(HOR^4) = \frac{3(FW_{HOR^4})}{x(FW_x) + w(FW_w) + y(FW_y)} \times 100$$

Figure 2:
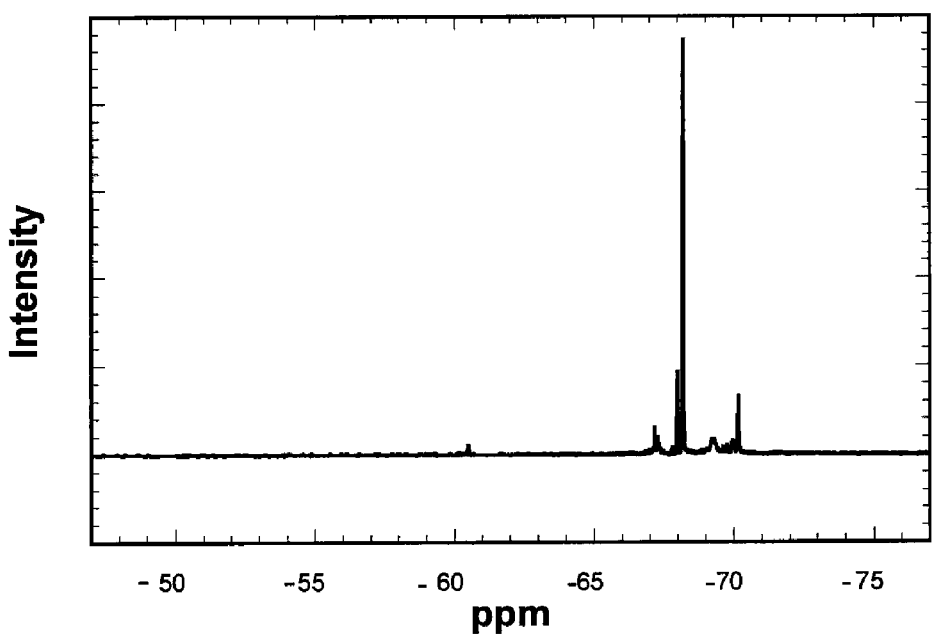
FIG. 2 illustrates an NMR analysis of the $^{29}$Si content of an exemplary mixture of alkoxy-modified silsesquioxanes according to the present invention, showing a broad spectral range from about −47 ppm to about −71 ppm. This NMR is that of Sample 2L, tabulated in Table 6 in the Examples.

The alkoxy-modified silsesquioxanes made using these methods consist essentially of "open" structures having the reactive alkoxysilyl group and are essentially free of pure closed caged polyhedral organosilsesquioxanes (POSS) structures that are known for use as nanoparticle fillers in various compounds. For example, a nuclear magnetic resonance (NMR) analysis of the $^{29}Si$ content of an exemplary oligomer mixture is illustrated in FIG. 2 shows a broad range (in parts per million, ppm) from about −47 ppm to about −71 ppm. In comparison, NMR analysis of the $^{29}Si$ content of a pure closed caged POSS structure (FIG. 1) shows a definitive peak at about −68 ppm. In FIG. 1, the POSS structure is a mixture of closed polyhedral $Si_8O_{12}$ ($T_8$), $Si_{10}O_{15}$ ($T_{10}$) and $Si_{12}O_{18}$ ($T_{12}$) structures obtained from Hybrid Plastics, Fountain Valley, Calif. In Table 6, discussed below, the $^{29}Si$ NMR ranges in ppm for exemplary oligomeric AMS and co-AMS products prepared show minor peaks in the range of −67 ppm to −77 ppm that can result from shifting of the silicon atoms due to the presence of the various R groups attached to the structures. However, without being bound by theory, it is believed that the method of preparation of the AMS and co-AMS products, described above, precludes or minimizes the formation of pure POSS structures because of the myriad of different geometric attachments that the rapid condensation of a trialkoxysilane generates. NMR spectra ranges for the amount of $^1H$ and/or $^{13}C$ in the products can also be determined, but these spectra will differ, depending on the various R groups attached to the structures, and are not illustrated here.

Another important feature of each of the AMS or co-AMS products produced is that the reactive alkoxysilyl group is present in such a small amount that only a small amount of alcohol can be liberated by hydrolysis of the product. That is, the y alkoxysilyl group generates only about 0.05% to about 10% by weight alcohol when the product is treated by substantially total acid hydrolysis. Suitably, the amount of generated alcohol is about 0.5% to about 8% by weight and, suitably, the amount of generated alcohol is about 1% to about 6% by weight.

Therefore, the AMS or co-AMS product(s) produced are very suitable for use in rubber compositions in which silica is employed as a reinforcing filler. In particular, the reactive alkoxysilane group(s) attached to the AMS or co-AMS products can participate in the alkoxysilane-silica reaction and could improve silica dispersion in the rubber. As discussed above, the alkoxysilane-silica reaction produces alcohol as a by-product when alkyltrialkoxysilanes and/or alkoxysilane-terminated polymer groups are used for silica dispersion in rubber compounds. Usually, the trialkoxysilane employed is a triethoxysilane or a trimethoxysilane, and the generated alcohol is ethanol or methanol, respectively. Because these alcohol emissions add to the VOC emissions generated from processing of the other rubber tire components, the amount of reinforcing silica and concomitant amount of trialkoxysilane employed is governed and limited by government environmental regulations.

Without being bound by theory, it was believed that the limited amount of alcohol that is available in the AMS or co-AMS product(s) might make these compounds very useful in rubber compounds because they have the potential to significantly reduce the level of potential VOCs emitted as alcohol during compounding and further processing. Moreover, it was believed that the limited amount of available unreacted alkoxysilane groups during and after mixing, could severely limit the degree of blistering in the vulcanized rubber compounds and tires made from them. Moreover, it was believed that the use of the products of the invention could allow a significant increase in the amount of silica used for reinforcement.

The use of the AMS and/or co-AMS products in rubber compounds not only minimizes alcohol emissions during compounding and further processing of the rubber, but these products also perform well as silica dispersing agents, giving improved physical properties to the stocks containing the compounds. In particular, as described in the examples below, rubber stocks containing AMS, and no other silica-dispersing agent, had a lower tan δ at 50° C. than comparable stocks containing an alkyltrialkoxysilane or a bis(trialkoxysilylorgano) disulfide or a mercaptotrialkoxysilane as silica dispersing or coupling agent, indicating reduced hysteresis and improved rolling resistance in tire treads made from these AMS-containing stocks. Other mechanical and dynamic viscoelastic physical properties of the AMS-containing stocks were acceptable when compared to the comparison stocks indicating that the improved properties were obtained without significantly affecting other physical properties. Similar results were obtained when a co-AMS product containing a mercapto group was used as a silica dispersing aid in rubber compounds.

Further, the use of a strong base catalyst for the alkoxysilane-silica reaction in AMS and co-AMS-containing rubber compounds produced rubber stocks having enhanced rubber reinforcement, increased polymer-filler interaction and lower compound viscosity. Moreover, the use of a catalyst further lowered the tan δ at 50° C. and the G' at −20° C. (an indicator of improved snow traction). Therefore, the combination of a catalyst with the AMS or co-AMS silica shielding agents produces rubber compounds that provide improved silica dispersion, wet and snow traction, lower rolling resistance and decreased hysteresis in tire treads containing such compounds.

It was also discovered that the amount of alcohol released from the rubber compounds as VOC during compounding and further processing is zero to about 0.1% by weight, often zero to about 0.05% by weight of the rubber compound.

A vulcanizable rubber compound as described herein comprises (a) an elastomer; (b) a reinforcing filler comprising silica or a mixture thereof with carbon black; (c) a silica dispersing aid comprising an alkoxy-modified silsesquioxane that comprises one or more compounds selected from the group consisting of alkoxy-modified silsesquioxanes having the formula

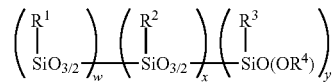

and mixtures thereof, wherein w, x and y represent mole fractions, y does not equal zero, either w or x but not both can be zero, and $w+x+y=1.00$, wherein $R^1$, $R^2$ and $R^3$ are the same or different and selected from the group consisting of (i) H or an alkyl groups having one to about 20 carbon atoms, (ii) cycloalkyl groups having 3 to about 20 carbon atoms, (iii) alkylaryl groups having 7 to about 20 carbon atoms, and (iv) $R^5X$, wherein X is selected from the group consisting of Cl, Br, SH, $S_aR^6$, $NR^6{}_2$, $OR^6$, $CO_2H$, $SCOR^6$, $CO_2R^6$, OH, olefins, epoxides, amino groups, vinyl groups, acrylates and methacrylates, wherein a=1 to about 8, $R^5$ is selected from the group consisting of alkylene groups having one to about 20 carbon atoms, cycloalkylene groups having 3 to about 20 carbon atoms, and $R^4$ and $R^6$ are selected from the group consisting of alkyl groups having one to about 5 carbon atoms, cycloalkyl groups having 3 to about 20 carbon atoms and alkylaryl groups having 7 to about 20 carbon atoms; (d) optionally about 0.05 to about 3% of a sulfur containing coupling agent, based on the silica; (e) optionally a catalyst for an alkoxysilane-silica reaction; and (f) a cure agent.

Because the alkoxy-modified silsesquioxane compounds contain such a small amount of the alkoxysilane y group and, thus, present a significant reduction in the alcohol that can be emitted during the alkoxysilane-silica reaction, the amount of silica present in the compound can, if desired, be significantly increased from amounts in current usage. That is, the silica can be present in an amount of about 15 per hundred parts rubber (phr) to about 200 phr or more. The silica can also be present in an amount of about 15 phr to about 150 phr, about 15 phr to about 120 phr, about 30 phr to about 90 phr, about 60 phr to about 80 phr, and the like. The alkoxy-modified silsesquioxane can be present in an amount of about 0.1% to about 20% by weight based on the silica. The alkoxy-modified silsesquioxane can also be present in an amount of about 0.2 to about 15%, about 0.5 to about 10%, or about 1 to about 6% by weight based on the silica.

Although not necessary for improvement in rubber properties, it may be desirable that the at least one of the $R^1$, $R^2$ and $R^3$ groups of the alkoxy-modified silsesquioxane is a group that binds to the elastomer. Such groups include, but are not limited to, acrylates, methacrylates, amino, vinyl, mercapto, sulfur and sulfide groups, and the like. Optionally, the reaction with the living end of a polymer after anionic polymerization can couple the alkoxy-modified silsesquioxane to the polymer. Further, the at least one of the $R^1$, $R^2$ and $R^3$ groups of the alkoxy-modified silsesquioxane can be, but is not limited to, a mercaptoalkyl group, a blocked mercaptoalkyl group, and an organo group containing a chain of about 2 to about 8 sulfur atoms, and the like.

Alternatively, or in addition to one or more groups that bind to the elastomer, the rubber compound can optionally contain an added sulfur containing coupling agent, such as, but not limited to mercaptoalkyltrialkoxy silanes, blocked mercaptoalkyltrialkoxy silanes, mercaptoalkylsilanes bound to silica, blocked mercaptoalkylsilanes bound to silica, bis(trialkoxysilylorgano) tetrasulfides or disulfides, and the like, in an amount of about 0.05 to about 3% based on the silica. A particularly useful commercial product containing a mercaptosilane supported on silica is available from PPG Industries, as Ciptane® 255LD that is a mercaptosilane fixed to silica with substantially no trialkoxysilane present. When this product is used, the amount of silica in the rubber compound can be adjusted for the added silica from the Ciptane® to make the desired total amount of silica.

The optional catalyst for the alkoxysilane-silica reaction can include strong organic and inorganic bases. Strong organic bases suitable for use as a catalyst in the invention preferably have a $pK_a$ in aqueous media of greater than about 10, more preferably greater than about 11 and, optimally, greater than about 12. The strong base can be present in the compound in an amount of about 0.01% to about 10%, typically about 0.1% to about 5%, based on the weight of the silica. For example, the catalytic amount of the strong organic base is typically about 0.003 per hundred parts rubber (phr) to about 8 phr, typically about 0.03 phr to about 4 phr. Exemplary strong organic bases for use in the invention compounds include, but are not limited to, strong alkali metal alkoxides, such as sodium or potassium alkoxide; guanidines, such as triphenylguanidine (TPG), diphenylguanidine (DPG), di-o-tolylguanidine (DTG), N,N,N',N'-tetramethylguanidine (TMG), and the like; and hindered amine bases, such as 1,8-diazabicyclo[5.4.0]undec-7-ene (DBU), 1,5-diazabicyclo[4.3.0]non-5-ene (DBN), and the like, tertiary amine catalysts, such as N,N-dimethylcyclohexylamine, triethylenediamine, triethylamine, and the like, quaternary ammonium bases, such as tetrabutylammonium hydroxide, bis-aminoethers, such as bis(dimethylaminoethyl)ethers, and the like, nitrogen-containing heterocycles such as, but not limited to, such heterocycles having from 5 to 7 ring members. A non-limiting example of a nitrogen-containing heterocycle is a substituted or unsubstituted imidazole such as, but not limited to, imidazole, 4-ethylamino imidazole, 2-mercapto-1-methyl imidazole, 1-methyl imidazole, 2,4,5-triphenyl imidazole, 2-methyl imidazole, 2-ethyl-4-methyl imidazole, 2-heptadecyl imidazole, and the like.

Suitable catalysts for alkoxysilane-silica reaction can further include alkyl tin compounds such as, but not limited to, butyl tin tris(2-ethylhexanoate), bis(2-ethyl-hexanoate) tin, butyl tin chloride dihydroxide, butyl tin hydroxide oxide hydrate, dibutyl tin dilaurate, dibutyl tin dimaleate, dibutyl tin oxide, and the like. A catalytic amount of the alkyl tin compound can be about 0.01% to about 5% by weight, suitably about 0.05% to about 3% by weight, and about 0.1% to about 2% by weight, based on the weight of the silica.

Additional suitable catalysts for alkoxysilane-silica reaction can further include zirconium compounds. Examples of suitable zirconium catalysts include, but are not limited to, zirconium 2-ethylhexanoate, zirconium tetrakis-(2-ethylhexanoate), tetraoctyl zirconate, zirconium n-butoxide, zirconium t-butoxide, zirconium di-n-butoxide (bis-2,4-pentanedionate), zirconium diisopropoxide bis(2,2,6,6-tetramethyl-3,5-heptanedionate), zirconium ethoxide, zirconium 2-ethylhexoxide, zirconium 3,5-heptanedionate, zirconium isopropoxide, zirconium 2-methyl-2-butoxide, zirconium 2,4-pentanedionate, zirconium n-propoxide, and the like. A catalytic amount of the zirconium compound can be about 0.01% to about 5% by weight, suitably about 0.05% to about 3% by weight, and about 0.1% to about 2% by weight, based on the weight of the silica.

Additional suitable catalysts for alkoxysilane-silica reaction can further include titanium compounds. Examples of suitable titanium catalysts include, but are not limited to, titanium trimethylsiloxide, titanium (isopropoxide)$_2$(2,4-pentandionate)$_2$, titanium (butoxide)$_2$(2,4-pentandionate)$_2$, titanium (isopropoxide)$_2$(ethyl-acetoacetate)$_2$, and the like. A catalytic amount of the titanium compound can be about 0.01% to about 5% by weight, suitably about 0.05% to about 3% by weight, and about 0.1% to about 2% by weight, based on the weight of the silica.

It is recognized that suitable catalysts can be mixtures of any of the above categories and subcategories.

The vulcanizable rubber compound optionally can also include a non-alkoxysilane silica shielding agent such as, but not limited to, glycols such as diethylene glycols, polyethylene glycols, and the like, fatty acid esters of hydrogenated or non-hydrogenated $C_5$ or $C_6$ sugars, polyoxyethylene derivatives of fatty acid esters of hydrogenated or non-hydrogenated $C_5$ or $C_6$ sugars, and mixtures thereof, or mineral or non-mineral additional fillers, as described in greater detail below. Further examples of non-alkoxysilane silica shielding agents can be found in U.S. Pat. Nos. 6,221,943 and 6,384,117, both of which are incorporated herein by reference.

Exemplary fatty acid esters of hydrogenated and non-hydrogenated $C_5$ and $C_6$ sugars (e.g., sorbose, mannose, and arabinose) that are useful as noalkoxysilane silica dispersing aids include, but are not limited to, the sorbitan oleates, such as sorbitan monooleate, dioleate, trioleate and sesquioleate, as well as sorbitan esters of laurate, palmitate and stearate fatty acids. Fatty acid esters of hydrogenated and non-hydrogenated $C_5$ and $C_6$ sugars are commercially available from ICI Specialty Chemicals (Wilmington, Del.) under the trade name SPAN®. Representative products include SPAN® 60 (sorbitan stearate), SPAN® 80 (sorbitan oleate), and SPAN® 85 (sorbitan trioleate). Other commercially available fatty acid esters of sorbitan are also available, such as the sorbitan monooleates known as Alkamul® SMO; Capmul® O; Glycomul® 0; Arlacel® 80; Emsorb® 2500; and S-Maz® 80. A useful amount of these optional silica dispersing aids is about 0.1% to about 25% by weight based on the weight of the silica, with about 0.5% to about 20% by weight being suitable, and about 1% to about 15% by weight based on the weight of the silica also being suitable.

Exemplary polyoxyethylene derivatives of fatty acid esters of hydrogenated and non-hydrogenated $C_5$ and $C_6$ sugars include, but are not limited to, polysorbates and polyoxyethylene sorbitan esters, which are analogous to the fatty acid esters of hydrogenated and non-hydrogenated sugars noted above except that ethylene oxide groups are placed on each of the hydroxyl groups. Representative examples of polyoxyethylene derivatives of sorbitan include POE® (20) sorbitan monooleate, Polysorbate® 80, Tween® 80, Emsorb® 6900, Liposorb® O-20, T-Maz® 80, and the like. The Tween® products are commercially available from ICI Specialty Chemicals. Generally, a useful amount of these optional silica dispersing aids is about 0.1% to about 25% by weight based on the weight of the silica, with about 0.5% to about 20% by weight being suitable, and about 1% to about 15% by weight based on the weight of the silica also being suitable.

The vulcanizable rubber compounds are compounded with reinforcing fillers, such as silica, or a mixture of silica and carbon black. Examples of suitable silica reinforcing fillers include, but are not limited to, precipitated amorphous silica, wet silica (hydrated silicic acid), dry silica (anhydrous silicic acid), fumed silica, calcium silicate, and the like. Other suitable fillers include aluminum silicate, magnesium silicate, and the like. Among these, precipitated amorphous wet-process, hydrated silicas are preferred. These silicas are so-called because they are produced by a chemical reaction in water, from which they are precipitated as ultrafine, spherical particles. These primary particles strongly associate into aggregates, which in turn combine less strongly into agglomerates. The surface area, as measured by the BET method gives the best measure of the reinforcing character of different silicas. For silicas of interest for the present invention, the surface area should be about 32 $m^2/g$ to about 400 $m^2/g$, with the range of about 100 $m^2/g$ to about 250 $m^2/g$, being preferred, and the range of about 150 $m^2/g$ to about 220 $m^2/g$ being most preferred. The pH of the silica filler is generally about 5.5 to about 7 or slightly over, preferably about 5.5 to about 6.8.

Some of the commercially available silicas that can be used include, but are not limited to, Hi-Sil® 190, Hi-Sil® 210, Hi-Sil® 215, Hi-Sil® 233, Hi-Sil® 243, and the like, produced by PPG Industries (Pittsburgh, Pa.). A number of useful commercial grades of different silicas are also available from Degussa Corporation (e.g., VN2, VN3), Rhone Poulenc (e.g., Zeosil® 1165 MP), and J.M. Huber Corporation.

The elastomers can be compounded with all forms of carbon black in a mixture with the silica. The carbon black can be present in amounts ranging from about one to about 50 phr, about five to about 35 phr, and the like. The carbon blacks can include any of the commonly available, commercially-produced carbon blacks, but those having a surface area (EMSA) of at least 20 $m^2/g$ and, more preferably, at least 35 $m^2/g$ up to 200 $m^2/g$ or higher are preferred. Surface area values used in this application are determined by ASTM D-1765 using the cetyltrimethyl-ammonium bromide (CTAB) technique. Among the useful carbon blacks are furnace black, channel blacks and lamp blacks. More specifically, examples of useful carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which can be utilized include acetylene blacks. A mixture of two or more of the above blacks can be used in preparing the carbon black products of the invention. Typical suitable carbon blacks are N-110, N-220, N-339, N-330, N-351, N-550, N-660, as designated by ASTM D-1765-82a. The carbon blacks utilized in the preparation of the vulcanizable elastomeric compositions of the invention can be in pelletized form or an unpelletized flocculent mass. Preferably, for more uniform mixing, unpelletized carbon black is preferred.

Certain additional fillers can be utilized according to the present invention as processing aids, including mineral fillers, such as clay (hydrous aluminum silicate), talc (hydrous magnesium silicate), aluminum hydrate $[Al(OH)_3]$ and mica, as well as non-mineral fillers such as urea and sodium sulfate. Preferred micas principally contain alumina and silica, although other known variants are also useful. The foregoing additional fillers are optional and can be utilized in the amount of about 0.5 to about 40 phr, about one to about 20 phr and, about one to about 10 phr, and the like.

In one embodiment of the invention, the vulcanizable compound of the invention is prepared by the steps of (a) mixing together at a temperature of about 130° C. to about 200° C. (drop temperature) in the absence of added sulfur and cure agents, a elastomer, a reinforcing filler comprising silica or a mixture thereof with carbon black, one or more alkoxy-modified silsesquioxanes, optionally the sulfur containing coupling agent, and optionally a catalyst for an alkoxysilane-silica reaction; (b) allowing the mixture to cool below the mixing temperature; (c) mixing the mixture obtained in step (b), at a temperature lower than a vulcanization temperature, with a cure agent and an effective amount of sulfur to achieve a satisfactory cure; and (d) curing the mixture obtained in step (c). The compound is usually cured at about 140° C. to about 190° C. for about 5 to about 120 minutes. The drop temperature for mixing together the components also can be about 145° C. to about 190° C. or about 155° C. to about 180° C.

The initial mixing step can include at least two substeps. That is, the initial mixing step can comprise the substeps of (i) mixing together at a temperature of about 130° C. to about 180° C., the elastomer, at least a portion of the silica, at least a portion of the alkoxy-modified silsesquioxanes, at least a portion of the optional catalyst, and at least a portion of the optional sulfur containing coupling agent (ii) cooling the mixture below the mixing temperature; and (iii) mixing the mixture obtained in step (ii) with the remainder of the silica, if any, the remainder, if any of the alkoxy-modified silsesquioxanes, the remainder, if any of the optional catalyst, and the remainder, if any, of the optional sulfur containing coupling agent, at a temperature of 130° C. to about 180° C. The temperatures achieved by the at least two substeps can be the same or different from each other, within the temperature range. If the optional sulfur containing coupling agent is employed in either substep, a suitable temperature range is about 130° C. to about 180° C.

The method can further include a remill step in which either no ingredients are added to the first mixture, or non-curing ingredients are added, in order to reduce the compound viscosity and improve the dispersion of the silica reinforcing filler. The drop temperature of the remill step is typically about 130° C. to about 175° C., especially about 145° C. to about 165° C.

The final step of the mixing process is the addition of cure agents to the mixture, including an effective amount of sulfur to achieve a satisfactory cure of the final compound.

Optionally, additional catalyst can be added to promote the reaction between the alkoxy-modified silsesquioxanes and the silica filler. The temperature at which the final mixture is mixed must be below the vulcanization temperature in order to avoid unwanted precure of the compound. Therefore, the temperature of the final mixing step should not exceed about 120° C. and is typically about 40° C. to about 120° C., suitably about 60° C. to about 110° C. and, especially, about 75° C. to about 100° C.

Based on the disclosure contained herein, and in the examples of invention compositions described below, one skilled in the art of rubber compounding can easily determine the effective amount of sulfur required for a satisfactory cure of the compound without undue experimentation. The additional sulfur can take any form, including soluble sulfur, insoluble sulfur, or any of the sulfur-donating compounds described as vulcanizing agents below, or mixtures of the foregoing.

The present invention can be used in conjunction with any solution polymerizable or emulsion polymerizable elastomer. Solution and emulsion polymerization techniques are well known to those of ordinary skill in the art. For example, conjugated diene monomers, monovinyl aromatic monomers, triene monomers, and the like, can be anionically polymerized to form conjugated diene polymers, or copolymers or terpolymers of conjugated diene monomers and monovinyl aromatic monomers (e.g., styrene, alpha methyl styrene and the like) and triene monomers. Thus, the elastomeric products can include diene homopolymers from monomer A and copolymers thereof with monovinyl aromatic monomers B. Exemplary diene homopolymers are those prepared from diolefin monomers having from about four to about 12 carbon atoms. Exemplary vinyl aromatic copolymers are those prepared from monomers having from about eight to about 20 carbon atoms. Copolymers can comprise from about 99 percent to about 50 percent by weight of diene units and from about one to about 50 percent by weight of monovinyl aromatic or triene units, totaling 100 percent. The polymers, copolymers and terpolymers of the present invention can have 1,2-microstructure contents ranging from about 10 percent to about 80 percent, with the preferred polymers, copolymers or terpolymers having 1,2-microstructure content of from about 25 to 65 percent, based upon the diene content. The elastomeric copolymers are preferably random copolymers which result from simultaneous copolymerization of the monomers A and B with randomizing agents, as is known in the art.

Particularly suitable rubber polymers for use in a vulcanized elastomeric compound of the invention include of styrene/butadiene copolymer, polyisoprene, polybutadiene, butadiene/isoprene copolymer, butadiene/isoprene/styrene terpolymers, isoprene/styrene copolymer, natural rubber, butyl rubber, halobutyl rubber, ethylene-propylene-diene rubber and combinations thereof.

The conjugated diene polymers, or copolymers or terpolymers of conjugated diene monomers and monovinyl aromatic monomers, can be utilized as 100 parts of the rubber in the treadstock compound, or they can be blended with any conventionally employed treadstock rubber which includes natural rubber, synthetic rubber and blends thereof. Such rubbers are well known to those skilled in the art and include synthetic polyisoprene rubber, styrene-butadiene rubber (SBR), styrene-isoprene-butadiene rubber, styrene-isoprene rubber, butadiene-isoprene rubber, polybutadiene, butyl rubber, neoprene, ethylene-propylene rubber, ethylene-propylene-diene rubber (EPDM), acrylonitrile-butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene-propylene rubber and the like. When the vulcanizable elastomeric composition of the present invention is blended with conventional rubbers, the amounts can vary widely with a lower limit comprising about ten percent to 20 percent by weight of the total rubber. The minimum amount will depend primarily upon the physical properties desired.

Vulcanized elastomeric compounds of the invention are prepared by the method described above. It is readily understood by those having skill in the art that the rubber compound would be compounded by methods generally known in the rubber compounding art, such as mixing the various vulcanizable polymer(s) with various commonly used additive materials such as, for example, curing agents, activators, retarders and accelerators, processing additives, such as oils, resins, including tackifying resins, plasticizers, pigments, additional fillers, fatty acid, zinc oxide, waxes, antioxidants, anti-ozonants, and peptizing agents. As known to those skilled in the art, depending on the intended use of the sulfur vulcanizable and sulfur vulcanized material (rubbers), the additives mentioned above are selected and commonly used in conventional amounts, in addition to other conventional rubber additives including, for example, other fillers, plasticizers, antioxidants, cure agents and the like, using standard rubber mixing equipment and procedures.

Such elastomeric compositions, when vulcanized using conventional rubber vulcanization conditions, exhibit reduced hysteresis, which means a product having increased rebound, decreased rolling resistance and lessened heat build-up when subjected to mechanical stress. Products including tires, power belts and the like are envisioned. Decreased rolling resistance is, of course, a useful property for pneumatic tires, both radial as well as bias ply types and thus, the vulcanizable rubber compositions of the present invention can be utilized to form treadstocks for such tires. Pneumatic tires can be made according to the constructions disclosed in U.S. Pat. Nos. 5,866,171; 5,876,527; 5,931,211; and 5,971,046, the disclosures of which are incorporated herein by reference. The composition can also be used to form other elastomeric tire components such as subtreads, sidewalls, body ply skims, bead fillers, apex, chafer, sidewall insert, wirecoat, inner liner, and the like Typical amounts of tackifier resins, if used, comprise about 0.5 to about 10 phr, usually about one to about 5 phr. Typical amounts of compounding aids comprise about one to about 50 phr. Such compounding aids can include, for example, aromatic, naphthenic, and/or paraffinic processing oils. Typical amounts of antioxidants comprise about 0.1 to about 5 phr. Suitable antioxidants, such as diphenyl-p-phenylenediamine, are known to those skilled in the art. Typical amounts of anti-ozonants comprise about 0.1 to about 5 phr.

Typical amounts of fatty acids, if used, which can include stearic acid, palmitic acid, linoleic acid or a mixture of one or more fatty acids, can comprise about 0.5 to about 3 phr. Typical amounts of zinc oxide comprise about one to about 5 phr. Typical amounts of waxes comprise about one to about 2 phr. Often microcrystalline waxes are used. Typical amounts of peptizers, if used, comprise about 0.1 to about 1 phr. Typical peptizers can be, for example, pentachlorothiophenol and dibenzamidodiphenyl disulfide.

The reinforced rubber compounds can be cured in a conventional manner with known vulcanizing agents at about 0.1 to 10 phr. For a general disclosure of suitable vulcanizing agents, one can refer to Kirk-Othmer, *Encyclopedia of Chemical Technology*, 3rd ed., Wiley Interscience, N.Y. 1982, Vol. 20, pp. 365 to 468, particularly "Vulcanization Agents and Auxiliary Materials," pp. 390 to 402. Vulcanizing agents can be used alone or in combination.

The vulcanization is conducted in the presence of a sulfur vulcanizing agent. Examples of suitable sulfur vulcanizing agents include "rubbermaker's" soluble sulfur; sulfur donating vulcanizing agents, such as an amine disulfide, polymeric polysulfide or sulfur olefin adducts; and insoluble polymeric sulfur. Preferably, the sulfur vulcanizing agent is soluble sulfur or a mixture of soluble and insoluble polymeric sulfur. The sulfur vulcanizing agents are used in an amount ranging from about 0.1 to about 10 phr, more preferably about 1.5 to about 7.5 phr, with a range of about 1.5 to about 5 phr being most preferred.

Accelerators are used to control the time and/or temperature required for vulcanization and to improve properties of the vulcanizate. The vulcanization accelerators used in the present invention are not particularly limited. Examples include thiazole vulcanization accelerators, such as 2-mercaptobenzothiazole, dibenzothiazyl disulfide, N-cyclohexyl-2-benzothiazole sulfenamide (CBS), N-tert-butyl-2-benzothiazole sulfenamide (TBBS), and the like; and guanidine vulcanization accelerators, such as diphenylguanidine (DPG) and the like. The amount of the vulcanization accelerator used is about 0.1 to about 5 phr, preferably about 0.2 to about 3 phr.

Pneumatic tires having improved tensile mechanical and dynamic viscoelastic properties, and comprising at least one component produced from the sulfur-vulcanized elastomeric compound of the invention exhibit provide improved silica dispersion, improved wet and snow traction, lower rolling resistance, increased rebound and decreased hysteresis in tire treads containing such compounds.

EXAMPLES

The following examples illustrate methods of preparation of representative alkoxy-modified silsesquioxanes, and rubber compounds and tire components containing them. However, the examples are not intended to be limiting, as other alkoxy-modified silsesquioxanes can be prepared according to the described methods. Moreover, the methods are exemplary only and other methods for preparing the alkoxy-modified silsesquioxanes, and other rubber compounds, including different compounding formulations, can be determined by those skilled in the art without departing from the scope of the invention herein disclosed and claimed.

In the examples below, the formula weights of the original silane and the perfect silsesquioxane that would be expected to form from the total hydrolysis reaction are as follows:

| R-Silane | Si—$X_3$ | R—$SiX_3$ (g/mol) | R—$SiO_{3/2}$ (g/mol) |
|---|---|---|---|
| octyl | triethoxy | 276.5 | 165.31 |
| octyl | trichloro | 247.7 | 165.31 |
| 3-mercapto propyl | trimethoxy | 196.3 | 127.23 |
| 3-chloro propyl | triethoxy | 240.8 | 129.62 |
| octanoyl 3-mercaptopropyl | triethoxy[a] | 364.6 | 253.44 |
| phenyl | triethoxy | 198.3 | 129.17 |

[a]NXT ™

These values were used along with the mole fractions of the silanes charged to determine the approximate theoretical yield for a desired AMS.

In each of the following examples, the amount of trialkoxysilane in each of the final AMS and/or co-AMS products was measured by the amount of alcohol recoverable from the product, according to the method published in Rubber Chemistry & Technology 75, 215 (2001). Briefly, a sample of the product was treated by total acid hydrolysis using a siloxane hydrolysis reagent (0.2 N toluenesulfonic acid/0.24 N water/15% n-butanol/85% toluene). This reagent quantitatively reacts with residual ethoxysilane (EtOSi) or methoxysilane (MeOSi), freeing a substantially total amount of ethanol or methanol that is then measured by a headspace/gas chromatographic technique, and expressed as the percentage by weight in the sample.

Similarly, in the examples illustrating rubber compounds made with the AMS and/or co-AMS products and silica filler, the amount of unreacted trialkoxysilane was determined for samples of the rubber after compounding and further processing, and expressed as the weight percent of alcohol obtained. The amount of alcohol potentially available for release into the environment as VOC was determined by subtraction. For example, a conventional silica dispersing agent octyl triethoxysilane (OTES) liberates 50.2 weight percent of alcohol upon complete hydrolysis. The alcohol potentially released as VOC during compounding is no more than 50.2% times the % OTES in the rubber compound minus the amount of alcohol released by hydrolysis of the rubber sample after compounding. Similar subtraction methods were used to calculate the released VOC from the AMS products during compounding, and to determine the VOC potentially released after subsequent processing.

Example 1

Preparation of n-Octyl Alkoxy-Modified Silsesquioxane (Octyl-AMS)

In three separate reactions, 11.06 g (40 mmol) of octyltriethoxysilane (OTES) was added to 155 mL of methanol containing 6.5 mL of 12N hydrochloric acid (A) (78 mmols) at 25° C. with stirring, (B) at 25° C. without stirring, and (C) at 60° C. without stirring. Each of these reactions gave almost identical high yields of product after 16 hrs. The majority of the product (~90%) was isolated by separation of the lower layer with a separator funnel. The remaining ~10% of the material was extracted with water and cyclohexane and drying at 50° C. and 0.1 mm of Hg vacuum for at least 6 hrs. A summary of these reactions is listed in Table 1.

TABLE 1

Example 1: Reaction Summary

| | Sample Number | | |
|---|---|---|---|
| | 1-A | 1-B | 1-C |
| OTES, g | 11.06 | 11.05 | 11.06 |
| MeOH, g | 121.84 | 121.74 | 121.74 |
| 12N HCl, g | 8.04 | 7.69 | 7.38 |
| Product separated from alcohol, g | 6.1 | 5.84 | 6.23 |
| Product in alcohol layer, g | 0.67 | 0.88 | 0.41 |
| Approximate total yield, % | 102 | 102 | 101 |

An analysis of samples of the individual products by weight percent (%) alcohol (ROH) that can be liberated by hydrolysis is presented in Table 2. $^1$H, $^{13}$C, and $^{29}$Si NMR spectra data showed that the products were essentially identical mixtures of alkoxy-modified silsesquioxanes having similar retained alkoxysilyl groups and, therefore, not possessing a POSS structure.

TABLE 2

Example 1: Sample Analysis

| | Sample Number | | |
|---|---|---|---|
| | 1-A | 1-B | 1-C |
| Ethanol hydrolyzed from | | | |
| Product in lower phase, % | 0.29 | 0.27 | 0.22 |
| Product from extraction, % | 0.2 | 0.057 | 0.22 |
| Combined products, % | 0.28 | 0.25 | 0.22 |
| Methanol hydrolyzed from | | | |
| Product in lower phase, % | 4.8 | 3.7 | 3.3 |
| Product from extraction, % | 1.4 | 0.59 | 7.2 |
| Combined products, % | 4.56 | 3.37 | 3.42 |

Without being bound by theory, it is believed that the high reaction rate and phase separation of the product prevented the synthesis of a closed cage POSS structure. Additional preparations illustrated in the examples below showed that the type of alcohol used, the presence and amount of added water, the use of a different siloxane organo group, and the catalyst level and type, could control the production of this type of product.

Example 2

Preparation of n-Octyl Alkoxy-Modified Silsesquioxane (Octyl-AMS) Via Semi-Continuous Synthesis In this example, 375 mL of absolute ethanol, 17.9 mL of 12N hydrochloric acid (0.215 mol) and 27.64 g (0.100 mol) of OTES were mixed in a 1 L separatory funnel and let stand at 25° C. As product was removed, more trialkoxysiloxane and water were added, as indicated in Table 3.

The initial slow reaction in ethanol was accelerated by the addition of water with the second trialkoxysiloxane addition. Additionally, the yield for each step increased with the increased concentration of the reactants and reaction time. All of the samples were dried in a warm vacuum oven (25° C. to 45° C.) for at least 1 hr at 0.1 mm of Hg to remove all traces of residual alcohol solvent. No additional catalyst or ethanol solvent was used for the subsequent preparation.

The percent of alcohol remaining at various stages is indicated. In particular, the weight % ethanol available upon hydrolysis in the starting reactant, OTES, is 50.2%. In sample 2C only 2.8% ethanol remained, sample 21 only 2.2% ethanol remained, the combined product 2A to 2K (2L) contained only 3.5% remaining ethanol, and the extracted product 2M contained only 2.8% remaining ethanol, thus showing the efficiency of this procedure in eliminating alcohol from the desired AMS product.

TABLE 3

Example 2: Preparation of AMS with in 375 mL of Ethanol and 17.9 mL of 12 N HCl (215 mmol)

| Sample No. | OTES (g) | Water (mL) | Time (hrs.) | Product (g) | TY[a] (g) | % of TY[a] | % EtOH |
|---|---|---|---|---|---|---|---|
| 2A | 27.64 (100 mmols) | 0 | 74 | 3.16 | 16.53 | 19.1 | |
| 2B | 27.65 | 13.43 | 24 | 8.97 | 16.65 | 54.3 | |
| 2C | 27.20 | 5 | 20 | 13.93 | 16.26 | 85.7 | 2.8 |
| 2D | 26.71 | 4 | 8 | 8.68 | 15.97 | 54.4 | |
| 2E | 27.25 | 2.78 | 16 | 9.54 | 16.29 | 58.6 | |
| 2F | 27.72 | 2.82 | 8 | 10.98 | 16.57 | 66.3 | |
| 2G | 27.83 | 2.88 | 16 | 20 | 16.64 | 120.2 | |
| 2H | 26.96 | 2.77 | 8 | 10.68 | 16.12 | 66.3 | |
| 2I | 51.51 | 5.79 | 62 | 42.27 | 30.8 | 137.3 | 2.2 |
| 2J | 55.99 | 5.94 | 24 | 23.37 | 33.48 | 69.8 | |
| 2K | | | 24 | 4.39 | | | |
| 2L (2A to 2K) | | | | 155.97 | 195.19 | 79.9 | 3.5 |
| 2M | Extract | | | 28.62 | | | 2.8 |
| 2N (Total) | | | | 184.59 | 195.19 | 94.6 | |

[a]TY is theoretical yield.

The $^1H$, $^{13}C$, and $^{29}Si$ NMR spectra for POSS and Sample 2L were determined. For easy characterization, the $^{29}Si$ NMR spectra are illustrated in FIGS. 1 and 2, respectively, and tabulated in Table 6. In particular, the $^{29}Si$ NMR spectra for Sample 2L indicated that the product is a mixture of partially hydrolyzed octyltriethoxysilane.

Example 3

Use of Octyltrichlorosilane

The procedure of Example 2 was used except no hydrochloric acid was added and the OTES was replaced with octyltrichlorosilane (OTCS) and water. The data in Table 4 illustrate the estimated weight of product formed as a function of time and the final total obtained after two OTCS additions.

TABLE 4

Example 3: Preparation of AMS in 375 mL of Ethanol and Octyl trichlorosilane (OTCS)

| Sample No. | OTCS (g) | Water (mL) | Time (hrs.) | Product (g) (cumulative) | TY[a] (g) | % of TY[a] | % EtOH |
|---|---|---|---|---|---|---|---|
| 3A | 24.80 | 15.5 | 3 | 0 | | 0 | |
| | | | 3.75 | 0.4 | | 2.4 | |
| | | | 4.75 | 2.88 | | 17.4 | |
| | | | 5.75 | 3.7 | | 22.4 | |
| | | | 20.75 | 7.77 | 16.55 | 46.9 | 4.39 |
| 3B | 24.80 | 2.7 | 0.5 | 0.08 | | 0.5 | |
| | | | 1 | 2.56 | | 15.6 | |
| | | | 1.75 | 17.92 | | 108.3 | |
| | | | 3.25 | 19.24 | | 116.2 | |
| | | | 18 | 25.13 | 16.55 | 151.8 | |
| 3 A&B | | | | 32.9 | 33.1 | 99.4 | 6.76 |

[a]TY is theoretical yield.

Figure 3:
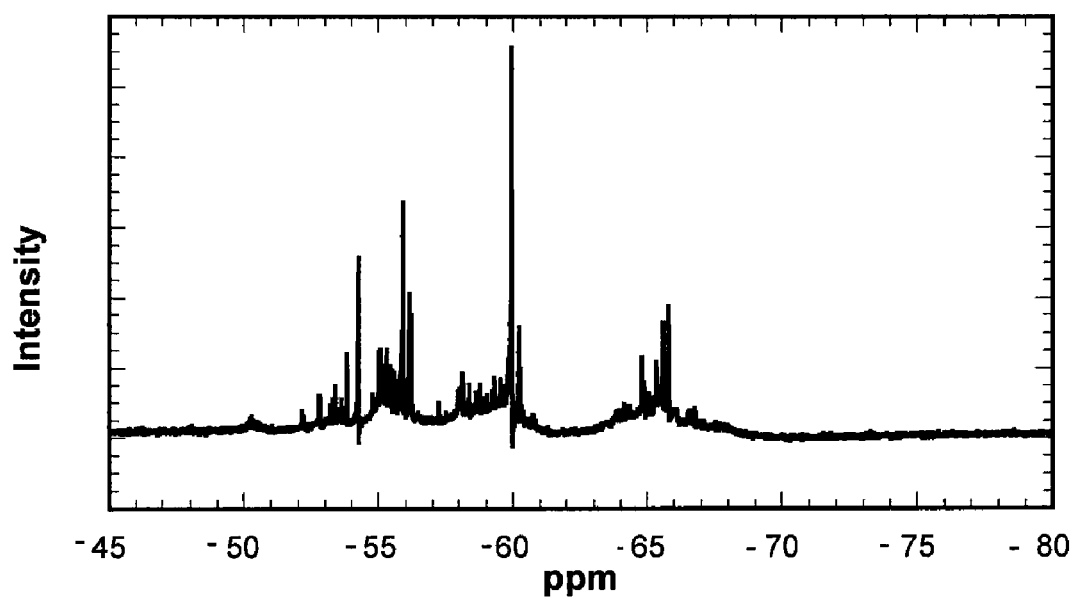
FIG. 3 illustrates an NMR analysis of the $^{29}$Si content of another exemplary mixture of alkoxy-modified silsesquioxanes according to the present invention, showing a broad spectral range from about −47 ppm to about −71 ppm. This NMR is that of Sample 3, tabulated in Table 6 in the Examples.

In this example, a product similar to that of Example 2 was obtained using the OTES precursor (OTCS) and aqueous ethanol. This was shown by the $^{29}Si$ NMR spectra illustrated in FIG. 3 and the alcohol analysis in Table 4. The rate of the reaction increased as more of the silane hydrolyzed to generate the hydrochloric acid catalyst.

Example 4

Preparation of 10 Mol % Mercapto Propyl Functionality on the Octyl Alkoxy-Modified Silsesquioxane (Co-AMS)

The reaction solvent mixture from Example 3 was further treated with an additional charge of 23.09 g of OTCS, 3 mL of water and 1.58 g (8 mmol) of 3-mercaptopropyl trimethoxysilane (MPS) to incorporate 10% mol of the mercaptopropyl functionality. A summary of the phase separated product that was obtained as a function of time is shown in Table 5.

TABLE 5

Example 4: Summary of phase separated product

| Silane | Si (mol) | Si (g) | Vol. (cc) | Water (cc add) | Time (hrs.) | Lo Phase (g) | TY (g) | % of TY |
|---|---|---|---|---|---|---|---|---|
| Octyl trichloro | 0.093 | 23.09 | 375 | 3 | 0.5 | 0.08 | 16.44 | 0.5 |
| | | | | | 1 | 2.95 | | 17.9 |
| | | | | | 1.5 | 7.96 | | 48.4 |
| | | | | | 2 | 13.34 | | 81.1 |
| | | | | | 2.75 | 14.42 | | 81.7 |
| | | | | | 65.75 | 18.8 | | 114.4 |

Figure 4:
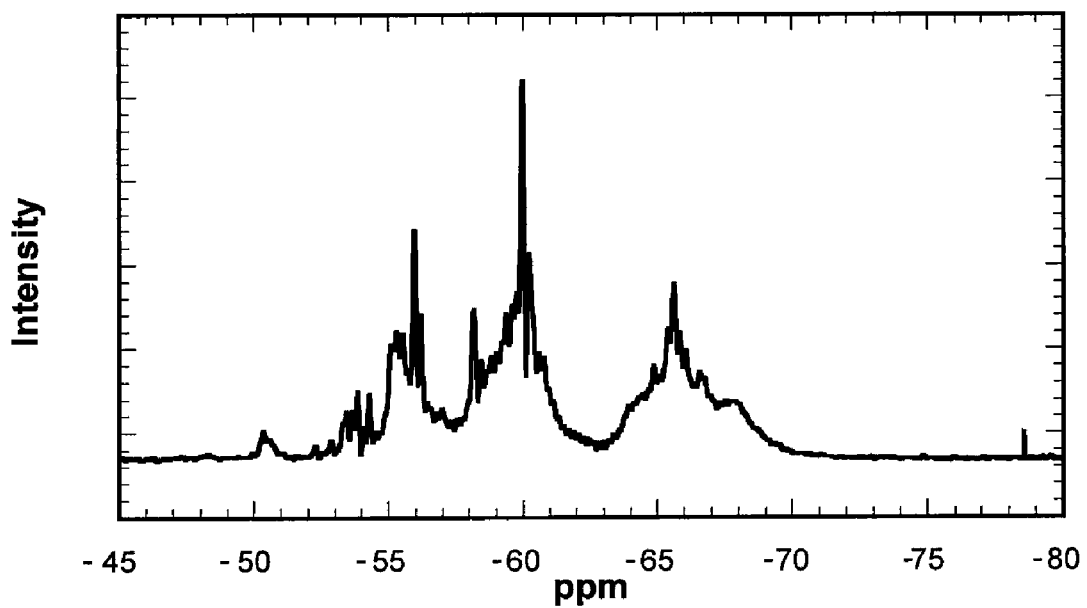
FIG. 4 illustrates an NMR analysis of the $^{29}$Si content of an exemplary mixture of co-alkoxy-modified silsesquioxanes according to the present invention, showing a broad spectral range from about −47 ppm to about −71 ppm. This NMR is that of Sample 4, tabulated in Table 6 in the Examples.

As illustrated in FIG. 4, the $^{29}Si$ NMR spectrum was consistent with the previous preparations of an open chain silsesquioxane and the $^1H$ and $^{13}C$ NMR spectra verified the incorporation of the MPS.

Example 5

Use of Basic Catalysts

High Levels of Sodium Hydroxide (5A)
The procedure of Example 2 was used with OTES (0.1 mol), except the hydrochloric acid catalyst was replaced with a solution of (0.228 mol) sodium hydroxide. Using this procedure the sodium salt of the hydrolyzed siloxane was rapidly formed overnight. This product was then isolated by neutralization reaction mixture and cyclohexane extraction. As illustrated in Table 6, a high yield was obtained that showed a $^{29}$Si NMR spectra indicating a higher level of complex cyclized condensation products. The retained ethanol level was 0.251%.

Catalytic Levels of Sodium Hydroxide (5B)

Using a catalytic level of sodium hydroxide (0.63 mmol), less of the insoluble sodium salt was slowly formed during a 72 hours reaction. The analysis, as performed above for (5A), gave almost identical results for yield and structure. However, the $^{29}$Si NMR indicated a slightly different mixture of condensation products was produced.

DBU, an Organic Strong Base (5C)

The procedure in (5A) above was repeated except that 3 g (2.07 mmol) of DBU (1,8-diazabicyclo[5.4.0]undec-7-ene) was used as a catalyst. An apparent gel product was obtained which became liquid after extraction with cyclohexane and hydrochloric acid. The yield was approximately 90% after vacuum drying. NMR analysis showed spectra similar to (5A) above and 1.68% ethanol was identified by total hydrolysis.

Example 6

Use of 3-Chloropropyl Triethoxysilane

Using 3-chloropropyl triethoxysilane (CPS) as the reactive siloxane as in example 2 gave a homogenous solution after 26 hours. The addition of more water to increase the reaction mixture to 30% gave the desired phase separation at about the same rate as previous preparations of highly condensed siloxanes. An alcohol level of 0.615% was measured and a $^{29}$Si NMR that was comparable to other acid catalyzed condensations.

Example 7

Partial Conversion of CPS Condensation Product to a Blocked Mercapto Functionality A solution of sodium thioacetic acid was prepared by adding 5.44 mL of thioacetic acid (5.81 g, 0.764 mol) to 28.5 mL of 21% sodium ethoxide in ethanol (24.74 g, 74 mmol) that had been cooled to 0° C. The pH was adjusted with the reagents to be in the 7 to 8 range. To this solution was added 50 mL of a cooled tetrahydrofuran (THF) solution containing 22 g (0.169 mol) of the CPS condensation product from Example 6. After warming to ambient temperature, the desired partially converted (~50%) blocked acetyl mercaptopropyl siloxane was obtained by water and cyclohexane extraction.

Example 8

Synthesis of AMS Using a (10%) Blocked Mercapto Alkoxysilane and Octyl Trialkoxysilane In a procedure similar to example 2, 43.69 g (0.157 mol) of OTES, 5.73 g (16 mmol) of NXT™ (Crompton Greenwich, Conn.) that is an octanoyl 3-mercaptopropyl triethoxysilane, and 26.8 mL (0.322 mol) of 12N hydrochloric acid were added to a 1 L separatory funnel. After overnight at ambient temperature, the lower phase was separated and vacuum dried to give 96% yield of the expected co-condensation siloxane from the reactants. Analysis showed 4.04% ethanol upon complete hydrolysis. The NMR was consistent with the previous acid catalyzed preparations. The resulting product was octyl-co-octanoyl blocked mercaptopropyl AMS (co-AMS-Oct-Mer)

Example 9

Preparation of a 33% Blocked Mercaptosilane Alkoxysilane Co-Condensate 27.67 g (0.10 mol) of OTES and 18.38 g (50 mmol) of NXT™ were added to the solvent mixture obtained in Example 8. Overnight, complete conversion to the 33% targeted co-condensate was obtained.

Example 10

Preparation of Co-Condensate from 10% MS in OTES

Using the procedures of Example 9, 52.65 g (0.190 mol) of OTES and 4.05 g (21 mmol) of 3-mercaptopropyl trimethoxysilane (MS) were added to a 1 L separatory funnel that contained 675 mL of the reaction solvent and a hydrochloric acid catalyst. After standing overnight the co-condensate containing 10-mol % MS was isolated and dried. Analysis showed 4.31% ethanol could be obtained from complete hydrolysis. The NMR spectrum showed the expected product.

Example 11

Preparation of Co-Condensate from 10% MS in Phenyl Triethoxysilane

In a procedure similar to Example 2, 49.11 g (0.248 mol) of phenyl triethoxysilane (PTMS), 6.42 g (33 mmol) of 3-mercaptopropyl trimethoxysilane (MS), 100 mL of water and 26.8 mL (0.322 mol) of 12N hydrochloric acid were added to a 1 L separatory funnel with 560 mL of absolute ethanol. No phase separation occurred overnight. An additional 150 mL of water was added to give a milky suspension of the condensate. After settling overnight at ambient temperature, the lower phase was separated and vacuum dried to give ~95% yield of the expected co-condensation siloxane from the reactants.

Example 12

Preparation of Co-Condensate from MS in Octyl Trichlorosilane

In a procedure similar to Example 3, 23.09 g (0.100 mol) of octyl trichlorosilane, 1.58 g (8 mmol) of 3-mercaptopropyl trimethoxysilane (MS), and 18.5 mL of water were added to a 1 L separatory funnel with 375 mL of ethanol. After shaking, the desired product was slowly formed as a cloudy insoluble material that then phase separated to the bottom of the funnel. After 3 days, both layers were clear and the product was isolated with a small amount of the reaction solvent to give 20.65 g of odorless octyl-co-mercaptopropyl AMS. Vacuum drying at 0.05 mm Hg with heating to 50° C. for 16 hours, gave an acid- and alcohol-free product. The NMR spectrum of the product was as expected. The product was octyl-co-mercaptopropyl AMS (co-AMS-Mer).

Example 13

$^{29}$Si NMR Analysis of the Condensed Siloxane Condensation Products

The products obtained in the above examples are condensation products of alkoxy-modified silsesquioxanes that have a multitude of structures and, as such, cannot be identified by a spectrum of one pure component. However, the strength of the $^{29}$Si NMR in different parts per million (ppm) regions can be used to characterize the distribution of the condensation products. For comparative purposes, the spectra, which encompass a −47 to −77 ppm range, were divided into the content for each 5 ppm section and compared to the more perfect POSS structures that have been obtained or reported in the literature. This comparison is illustrated in Table 6.

TABLE 6

Example 13: $^{29}$Si NMR Analysis

| Example # | −47 to −52 | −52 to −57 | −57 to −62 | −62 to −67 | −67 to −72 | −72 to −77 | Description |
|---|---|---|---|---|---|---|---|
| Comparison | 0.2 | 0.7 | 4.8 | 5.9 | 88.3 | 0.1 | POSS |
| 1 | 3.8 | 31.6 | 37.8 | 21.2 | 5.3 | 0 | HCl flask |
| 2L | 3.1 | 27.4 | 32.4 | 30.8 | 5.9 | 0.3 | HCl sep. f. |
| 2N | 1.1 | 34.7 | 30 | 26.9 | 7.2 | 0.2 | HCl sep. f. |
| 3 | 1.4 | 26.2 | 36 | 27.6 | 8.8 | 0 | SiCl3 |
| 4 | 1.9 | 23.1 | 39.6 | 27 | 8.4 | 0 | SiCl3 co MPS |
| 5A | 1.3 | 18.8 | 20.5 | 23 | 36.2 | 0.2 | NaOH |
| 6 | 0 | 8.5 | 20.8 | 49.6 | 20.9 | 0.2 | R = ClPr |
| 8 | 0.6 | 28.8 | 25.3 | 35.6 | 7.5 | 2.1 | 10% co NXT |
| 9 | 0.2 | 23.9 | 24.4 | 37.6 | 13.8 | 0 | 33% co NXT |
| 5C | 0.3 | 9.5 | 13.4 | 46 | 30.7 | 0.2 | DBU |

The area attributed to the pure closed POSS (polyhedral oligomeric silsesquioxane) structures can be seen as consisting of signals at less than −67 ppm and represents the pure 8 and 10 silicone containing rings. There is no alkoxysilane group remaining in the pure POSS structure. Chemical shifts in the NMR to greater than the −67 ppm are attributed to the myriad of structures that can be obtained from the condensation of a trialkoxy silane with itself. These structures have an open oligomeric arrangement in which some of the remaining alkoxysilane acts as a structure-controlling feature to prevent the formation of a highly stable and unreactive POSS arrangement of silicone and oxygen atoms. That is, the open oligomeric structures obtained in the present invention contain residual amounts of alkoxysilanes that are still reactive. The NMR data in the range of −67 to −72 and −72 to −77 range for these structures represent the shifting of the Si atom frequency depending on the catalyst and/or R group used. These structures are still open structures containing residual alkoxysilanes and these frequencies do not represent closed POSS structures.

Example 14

Evaluation of AMS in a Silica-Reinforced Rubber

The AMS product prepared in Example 2 was evaluated for use in a rubber composition. Three rubber stocks were compounded with silica and AMS (stock 1), OTES (comparison stock 2), or no silica coupling or silica dispersing additive (comparison stock 1), according to the formulations illustrated in Table 7.

All of the charges are listed as parts per hundred rubber (phr). The drop temperatures of the mixing steps were as follows: master batch 1, 160° C.; remill, 155° C.; and final, 110° C. All of the compounded final stocks were sheeted and subsequently annealed at 171° C. for 15 minutes. The annealing conditions employed were chosen to be similar to conventional curing conditions.

TABLE 7

Example 14: Rubber composition

| Ingredient | Amount (phr) |
|---|---|
| Master Batch 1 | |
| Solution styrene-butadiene rubber[a] | 100 |
| Precipitated Silica | 65 |
| n-octyl triethoxysilane, OTES | varied |

TABLE 7-continued

Example 14: Rubber composition

| Ingredient | Amount (phr) |
|---|---|
| n-Octylsilylsesquioxane (AMS) | varied |
| Aromatic Oil | 20 |
| Wax | 1.7 |
| Antioxidant[b] | 0.95 |
| Final | |
| Sulfur | 2.8 |
| Accelerator[c] | 1.17 |
| Zinc Oxide | 1.94 |
| Retarder[d] | 0.25 |
| Stearic Acid | 1.56 |
| Diphenyl guanidine | 0.39 |

[a]SSBR (23.5% styrene, $T_g$ −36° C., ML$_4$ 58);
[b]N-(1,3-dimethylbutyl)-N'-phenyl-p-phenylenediamine (6PPD);
[c]N-cyclohexyl-2-benzothiazole sulfenamide (CBS)
[d]N-(Cyclohexylthio)pthalimide (PVI)

Example 15

A determination of alcohol content was made for the green (uncured) and cured stocks. The amount of alcohol emitted as VOC during compounding of the green stocks was obtained by subtracting the amount of available alcohol remaining in each of the green stocks from the theoretical amount of alkoxysilane that could be hydrolyzed to alcohol originally introduced into the compounds by the silica dispersing agent employed. As illustrated by the results in Table 8, the green comparison stock 2 containing OTES retained about 50% of alkoxysilane that could be hydrolyzed to alcohol after compounding. The alcohol emitted as VOC during the compounding of the OTES-containing stock represent about 0.933% of the sample.

In contrast, the original AMS product from example 2 retained less than 3.5% available alcohol when it was introduced into the compounding mixture. As illustrated in Table 8, the alkoxysilane that could be hydrolyzed to alcohol in stock 3 was only 4% of what could be obtained from stock 2. Therefore, the amount of alcohol emitted as VOC during compounding was negligible. Moreover, the AMS-containing green stocks contained no further alcohol available for release as VOC during further processing of the rubber into tire components.

As discussed in the examples below, not only did the use of the AMS product solve the problem of additional VOC emissions during processing of the rubber product, the AMS also performed well as an silica dispersing agent, giving improved physical properties to the stocks containing this compound.

TABLE 8

Example 15: Properties of Rubber Compounded with Silica and the Shielding Agents

| Shielding Agent | Comparison Stock 1 (phr) | Comparison Stock 2: OTES (phr) | Stock 1: AMS (Ex 2L) (phr) |
|---|---|---|---|
| Alkyl alkoxysilane (OTES) | 0 | 6.65 | 0 |
| n-Octylsilylsesquioxane (AMS) | 0 | 0 | 4.10 |
| Alcohol that could be liberated by hydrolysis of the formulation | | 1.598% | 0.044% |
| Alcohol/VOC Emission | | | |
| Alcohol from alkoxysilane in green stock that could be hydrolyzed | 0 | 0.665% | 0.012% |
| Alcohol emitted as VOC for rubber stock (during compounding) | 0 | 0.933% | 0.032% |
| Physical Properties | | | |
| ML$_4$ at 130° C. | >222 | 52 | 58 |
| δ(ΔG'), MPa of annealed stocks | 6.68 | 1.92 | 3.23 |
| % Rebound at 50° C. | 52.0 | 35.4 | 41.8 |
| G' at −20° C., MPa | 75.61 | 33.57 | 42.99 |
| G' at 25° C., MPa | 17.25 | 5.14 | 6.89 |
| G' at 50° C., MPa | 14.33 | 4.00 | 5.36 |
| Temperature sweep tan δ at 0° C. | 0.2024 | 0.3270 | 0.2948 |
| Temperature sweep tan δ at 50° C. | 0.0806 | 0.1605 | 0.1347 |
| MTS compression test, tan δ at 0° C. | 0.1016 | 0.2774 | 0.2348 |
| MTS compression test, tan δ at 50° C. | 0.0471 | 0.2187 | 0.1579 |
| ΔG' (0.25%-14.5% E) at 50° C., MPa | 8.49 | 1.99 | 2.59 |

Example 16

The green stocks prepared as in Example 14 were characterized as to Mooney viscosity (ML$_4$). The Mooney viscosity measurement was conducted at 130° C. using a large rotor, and was recorded as the torque when rotor had rotated for 4 minutes. The stocks were preheated at 130° C. for 1 minute before the rotor was started.

As illustrated in Table 8, the rubber stock 1 containing AMS had a Mooney viscosity that was comparable with that of comparison stock 2 containing OTES, illustrating that AMS was performing comparably to OTES as a silica shielding agent during mixing of the compound. A reduced compound Mooney viscosity is advantageous because it provides better processability and handling, especially during the extrusion process. Comparison stock 1 did not contain a silica coupling agent or a silica shielding agent, resulting in a Mooney viscosity too high to be processed.

The dynamic viscoelastic mechanical properties of the cured stocks were obtained from strain and temperature sweep tests using a Rheometrics Dynamic Analyzer (Rheometrics Inc.). In particular, the storage modulus (G') at −20° C., 25° C. and 50° C., and the tan δ at 0° C. and 50° C. were obtained from temperature sweep tests conducted at a frequency of 31.4 radians/second using 0.5% strain for the temperatures ranging from −100° C. to −30° C. and 2+% strain for the temperatures ranging from −30° C. to +100° C. The strain sweep was conducted at 0° C. and 50° C. with a frequency of 0.5 Hz and a strain sweeping from 0.25% to 14.75% E.

The AMS containing stock had a lower tan δ at 50° C. than the OTES containing stock, indicating reduced hysteresis and improved rolling resistance in tire treads made from these stocks.

The hysteresis properties of the rubber stocks were also evaluated by dynamic compression testing (tan δ at 0° C. and 50° C.) using a MTS Elastomer Tester (MTS Inc.). The sample geometry for the dynamic compression testing is a 9.5 mm diameter by 15.6 mm length cylindrical button. The sample was compression under a static load of 2 kg before testing at 1 Hz with a dynamic compression load of 1.25 kg. The results of these tests were similar to those using the temperature sweep. The AMS containing stock again showed a lower tan at 50° C. than the OTES containing stock, confirming the reduced hysteresis and improved rolling resistance obtained above.

A good silica coupling or dispersing agent should disperse the silica during compounding and stabilize the filler morphology during storage and curing of the compounds. Therefore, the three stocks were examined for filler flocculation (the Payne effect, ΔG') before and after they were annealed at 171° C. for 15 minutes. The Payne effects of uncured stocks were obtained from strain sweep tests of the three stocks using a Rubber Process Analyzer (Alpha Technologies, Inc.), conducted at 50° C. at a frequency of 0.1 Hz, and a strain sweeping from 0.25% to 1000%. The annealed rubber compounds were cooled to 40° C. for 30 minutes before conducting the strain sweep test.

The filler flocculation behavior in all of the stocks were evaluated by examining the change in the Payne effect, δ (ΔG'), in the stocks containing no curatives, before and after the thermal annealing, where δ (ΔG') is defined as the ΔG' (with thermal annealing) minus the ΔG' (without thermal annealing). Thermal annealing at 171° C. for 15 minutes simulated the heat history normally encountered during vulcanization.

The ΔG' is well understood as a measure of filler networking. The measurement of δ(ΔG') allows assessment of the net increase in filler flocculation after annealing and the degree of strong polymer-filler linkages and silica hydrophobation (shielding) prior to annealing. The higher the degree of polymer-filler interaction and silica shielding in the rubber, the less the filler will flocculate upon heating.

The Payne effect of the AMS containing stock and the OTES containing stock is comparable and acceptable and significantly lower than that of the comparison stock containing no silica dispersing additive. The AMS can be seen as equivalent to OTES as a shielding agent.

As illustrated in Table 8, and discussed above, the AMS containing stock and the OTES containing stock had comparable mechanical and dynamic viscoelastic properties, with the unexpected and desirable exception that the AMS containing stock had reduced hysteresis as measured by the tan δ at 50° C.

Example 17

Evaluation of Co-AMS-Mercapto Compounds and an Imidazole Catalyst in Silica-Filled Rubbers The products obtained in Examples 8 and 10, octyl-co-octanoyl blocked mercaptopropyl AMS (co-AMS-Oct-Mer) and octyl-co-mercaptopropyl AMS (co-AMS-Mer), respectively, were compounded in rubber stocks. In this example, the use of a catalyst, imidazole, that promotes the reaction between the alkoxy-modified silsesquioxane and the silica filler, was also evaluated. The ingredients of the rubber compounds are listed in Table 9, as well as the drop temperatures for the master batch, remill and final stages. All of the compounded final stocks were sheeted and subsequently annealed at 171° C. for 15 minutes.

Example 18

The processability of rubber compounds were evaluated by examining the compound Mooney viscosity and curing properties. The Mooney viscosity was determined as described in Example 15. The $t_5$ is the time required to increase 5 Mooney units during the Mooney scorch measurement. It is used as an index to predict how fast the compound viscosity will rise during processes such as extrusion. The Monsanto Rheometer MD2000 was used to characterize the stock curing process with conditions of a frequency of 1.67 Hz and a strain of 7% at 160° C. The $t_{s2}$, $t_{10}$ and $t_{90}$, the times at which the torque rises to 2%, 10% and 90%, respectively, of the total torque increase during the curing process, were thus obtained. These times are used to predict how quickly the viscosity builds up ($t_{s2}$, $t_{10}$) and the curing rate ($t_{90}$) during the curing process.

The compound Mooney ($ML_4$) and curing characteristics of the stocks are illustrated in Table 10. The addition of the imidazole catalyst reduced the $ML_4$ and improved the $t_{90}$ of the co-AMS containing stocks 3 and 5, in comparison to the co-AMS containing stocks 2 and 4 that did not contain the imidazole.

TABLE 9

Example 18: Rubber Compositions

| Ingredient | Comparison Stock 3: S2 Silane (phr) | Stock 2: co-AMS-mercapto propyl-octyl (Ex 10) (phr) | Stock 3: co-AMS-mercapto propyl-octyl (Ex 10)/ Imidazole (phr) | Stock 4: co-AMS-block-mercapto propyl-octyl (Ex 8) (phr) | Stock 5: co-AMS-block-mercapto propyl-octyl (Ex 8)/ Imidazole (phr) |
|---|---|---|---|---|---|
| Master Batch 1 | | | | | |
| Natural Rubber | 25 | 25 | 25 | 25 | 25 |
| Solution styrene-butadiene rubber[1] | 75 | 75 | 75 | 75 | 75 |
| Precipitated Silica | 30 | 30 | 30 | 30 | 30 |
| Carbon Black | 35 | 35 | 35 | 35 | 35 |
| Naphthenic Oil | 15 | 13.5 | 13.5 | 13.5 | 13.5 |
| Disulfane silica coupling agent[2] | 2.64 | 0 | 0 | 0 | 0 |
| co-AMS-mercapto propyl-octyl (Ex 10) | 0 | 2.35 | 2.35 | 0 | 0 |
| co-AMS-block-mercapto propyl-octyl (Ex 8) | 0 | 0 | 0 | 2.11 | 2.11 |
| Imidazole | 0 | 0 | 1 | 0 | 1 |
| Wax | 1.0 | 1.0 | 1.0 | 1.0 | 1.0 |
| Stearic acid | 1.5 | 1.5 | 1.5 | 1.5 | 1.5 |
| Antioxidant[3] | 0.95 | 0.95 | 0.95 | 0.95 | 0.95 |
| (Drop Temp) | 154° C. | 160° C. | 160° C. | 160° C. | 160° C. |
| Remill | | | | | |
| (Drop Temp) | 146° C. | 146° C. | 146° C. | 146° C. | 146° C. |
| Final | | | | | |
| Sulfur | 1.56 | 1.78 | 1.78 | 1.78 | 1.78 |
| Zinc Oxide | 2.5 | 2.5 | 2.5 | 2.5 | 2.5 |
| Accelerator (CBS)[4] | 1.5 | 1.5 | 1.5 | 1.5 | 1.5 |
| Diphenyl guanidine | 0.5 | 0.5 | 0.5 | 0.5 | 0.5 |
| PVI | 0.25 | 0.25 | 0.25 | 0.25 | 0.25 |
| (Drop Temp) | 110° C. | 110° C. | 110° C. | 110° C. | 110° C. |

[1]SSBR (20% styrene, 48% vinyl, $T_g$ = −33° C., $ML_4$ = 92)
[2]S2 silane, Silquest A1589 from OSi Specialties
[3]N-(1,3-dimethylbutyl)-N'-phenyl-p-phenylenediamine (6PPD)
[4]N-cyclohexyl-2-benzothiazole sulfenamide (CBS)

TABLE 10

Example 18: The green stock Mooney viscosity and cure characteristics

| Stock Number | $ML_4$ at 130° C. | $t_5$ scorch @ 130° C. (seconds) | $t_{s2}$ @ 160° C. (min) | $t_{10}$ @ 160° C. (min) | $t_{90}$ @ 160° C. (min) |
|---|---|---|---|---|---|
| Comparison Stock 3: S2 Silane | 69.17 | 1470 | 4.77 | 4.45 | 15.37 |
| Stock 2: co-AMS-mercapto propyl-octyl (Example 10) | 84.84 | 985 | 3.17 | 2.63 | 26.16 |
| Stock 3: co-AMS-mercapto propyl-octyl (Example 10)/ Imidazole | 71.5 | 985 | 3.52 | 3.08 | 10.38 |
| Stock 4: Co-AMS-blocked-mercapto propyl-octyl (Example 8) | 70.65 | 1147 | 4.22 | 3.51 | 23.97 |
| Stock 5: Co-AMS-blocked-mercapto propyl-octyl (Example 8)/ Imidazole | 62.57 | 1262 | 4.6 | 4.22 | 10.21 |

Example 19

Filler flocculation behavior in all of the stocks were evaluated as disclosed in Example 16. As illustrated in Table 11, the filler flocculation was found to be largely suppressed by the presence of imidazole, as illustrated by a comparison of rubber stocks 3 and 5 containing the imidazole catalyst and rubber stocks 2 and 4 not containing the catalyst. These results suggest the presence of a higher degree of polymer-filler interaction, and/or a higher degree of silica hydrophobation in the rubbers containing added imidazole. These results are consistent with those findings in the preceding section.

TABLE 11

Example 19: The degree of filler flocculation

| Stock Number | Degree of filler flocculation $\delta$ ($\Delta G'$), kPa |
|---|---|
| Comparison Stock 3: S2 Silane | 2312 |
| Stock 2: co-AMS-mercapto propyl-octyl (Example 10) | 2055 |
| Stock 3: co-AMS-mercapto propyl-octyl (Example 10)/ Imidazole | 1327 |
| Stock 4: Co-AMS-blocked-mercapto propyl-octyl (Example 8) | 1407 |
| Stock 5: Co-AMS-blocked-mercapto propyl-octyl (Example 8)/ Imidazole | 995 |

Example 20

The dynamic viscoelastic mechanical properties of the stocks were obtained from the procedure described in example 16. As illustrated in Table 12, stocks 3 and 5 containing the imidazole catalyst had lower values of −20° C. G' and tan δ at 50° C. than the stocks 2 and 4 that did not contain the imidazole. Stocks 3 and 5 also had values of tan δ at 0° C. that were equivalent to stocks 2 and 4. The tan δ at 0° C. is used as a predictor of tire wet traction, the tan δ at 50° C. as a predictor of rolling resistance, and the G' at −20° C. as a predictor of snow traction. Therefore, it was predicted that the imidazole-containing stocks would have better wet and snow traction and lower rolling resistance, compared to the comparison stock that did not contain a co-alkoxy-modified silsesquioxane or a catalyst.

TABLE 12

The Viscoelastic properties measured by temperature sweep

| Stock Number | G' @ −20° C. (MPa) | tan δ @ 0° C. | tan δ @ 50° C. |
|---|---|---|---|
| Comparison Stock 3: S2 Silane | 30.37 | 0.3175 | 0.2119 |
| Stock 2: co-AMS-mercapto propyl-octyl | 25.69 | 0.2991 | 0.1859 |
| Stock 3: co-AMS-mercapto propyl-octyl/ Imidazole | 21.11 | 0.3244 | 0.1501 |
| Stock 4: Co-AMS-blocked-mercapto propyl-octyl | 26.84 | 0.3071 | 0.1887 |
| Stock 5: Co-AMS-blocked-mercapto propyl-octyl/ Imidazole | 22.83 | 0.3108 | 0.1461 |

Example 21

The resilience of the annealed rubber stocks was measured by the Zwick rebound resilience tester. The test piece was round, with a diameter of 38 mm and a thickness of 19 mm. This test piece was subjected to one half-cycle of deformation. That is, the test piece was strained by impacting it with an indentor which was free to rebound after the impact. Rebound resilience is defined as the ratio of mechanical energies before and after impact. The test samples were preheated to 50° C. for 30 minutes prior to testing.

The rebound test results are illustrated in Table 13. All of the co-AMS stocks had lower hysteresis than the comparison stock. The stocks 3 and 5 containing the imidazole catalyst had a higher resilience value (a lower hysteresis loss) than stocks 2 and 4 that did not contain the imidazole catalyst.

TABLE 13

Example 21: Rebound

| Stock Number | 50° C. Rebound |
|---|---|
| Comparison Stock 3: S2 Silane | 54.40 |
| Stock 2: co-AMS-mercapto propyl-octyl | 55.60 |
| Stock 3: co-AMS-mercapto propyl-octyl/ Imidazole | 59.80 |
| Stock 4: Co-AMS-blocked-mercapto propyl-octyl | 56.40 |
| Stock 5: Co-AMS-blocked-mercapto propyl-octyl/ Imidazole | 60.00 |

As illustrated by the test data in Examples 16 through 21, rubber stocks containing AMS and/or co-AMS with a catalyst such as imidazole have enhanced rubber reinforcement, increased polymer-filler interaction and lower compound viscosity. Therefore, use of the catalyst with the alkoxy-modified silsesquioxanesilica shielding agents produced tires having improved silica dispersion and wet and snow traction, lower rolling resistance and decreased hysteresis.

Example 22

Evaluation of AMS, AMS and a Mercaptosilane, and an Imidazole Catalyst in Silica-Filled Rubbers The AMS prepared in Example 2 was evaluated in compounding a silica and carbon black-containing rubber according to the method described in Example 14. The ingredients in the composition are listed in Table 14.

TABLE 14

Example 22: Rubber Compositions

| Ingredient | Comparison Stock 3: S2 silane (phr) | Comparison Stock 4: OTES & Mercapto-silane (phr) | Stock 6: AMS & Mercapto-silane (phr) | Stock 7: AMS & Mercapto-silane/ Imidazole (phr) |
|---|---|---|---|---|
| Solution styrene-butadiene rubber | 75 | 75 | 75 | 75 |
| Natural rubber | 25 | 25 | 25 | 25 |
| Precipitated Silica | 30 | 30 | 30 | 30 |
| Carbon Black | 35 | 35 | 35 | 35 |
| Naphthenic Oil | 15 | 13.5 | 13.5 | 13.5 |
| Disulfane silica coupling agent[1] | 2.64 | 0 | 0 | 0 |
| Octyltriethoxysilane (OTES) | | 3 | 0 | 0 |
| AMS from example 2L | 0 | 0 | 3 | 3 |
| Mercaptosilane[2] | 0 | 0.2 | 0.2 | 0.2 |
| Imidazole | 0 | 0 | 0 | 1 |
| Wax | 1.0 | 1.0 | 1.0 | 1.0 |
| Stearic acid | 1.5 | 1.5 | 1.5 | 1.5 |
| Antioxidant[3] | 0.95 | 0.95 | 0.95 | 0.95 |
| Sulfur | 1.56 | 1.78 | 1.78 | 1.78 |
| Zinc Oxide | 2.5 | 2.5 | 2.5 | 2.5 |
| Accelerator (CBS)[4] | 1.5 | 1.5 | 1.5 | 1.5 |
| Diphenyl guanidine | 0.5 | 0.5 | 0.5 | 0.5 |

[1]S2 silane, Silquest A1589 from OSi Specialties
[2]Ciptane ® 255 LD (PPG Industries), mercaptosilane fixed to silica with no trialkoxysilane present, in the amount of 6.67 phr that is equivalent to the mercaptosilane concentration of 0.2 phr. The amount of silica in the preparation was adjusted for the added silica from the Ciptane to make a total of 30 phr silica.
[3]N-(1,3-dimethylbutyl)-N'-phenyl-p-phenylenediamine (6PPD)
[4]N-cyclohexyl-2-benzothiazole sulfenamide (CBS)

TABLE 15

Example 22: Test Data

| Property | Comparison Stock 3: S2 silane (phr) | Comparison Stock 4: OTES & Mercapto-silane (phr) | Stock 6: AMS & Mercapto-silane (phr) | Stock 7: AMS & Mercapto-silane/ Imidazole (phr) |
|---|---|---|---|---|
| Rolling Resistance (tan δ at 50° C.) | | | | |
| Temperature Sweep 2% | 0.1693 | 0.1521 | 0.1606 | 0.1203 |
| Strain Sweep 2% E | 0.1649 | 0.1333 | 0.1226 | 0.09236 |
| Strain Sweep 2% RPA | 0.211 | 0.203 | 0.197 | 0.15 |
| MTS compression | 0.1621 | 0.1364 | 0.13 | 0.1092 |
| Rebound at 50° C. | 58.20 | 60.00 | 60.80 | 64.20 |
| Wet Traction (tan δ at 0° C.) | | | | |
| Temperature Sweep | 0.3237 | 0.3809 | 0.3584 | 0.3618 |
| Strain Sweep 2% E | 0.2307 | 0.2068 | 0.2079 | 0.161 |
| MTS compression | 0.2424 | 0.2392 | 0.2243 | 0.2092 |
| Snow Traction (G' at −20° C., MPa) | 34.37 | 22.64 | 16.69 | 14.4 |
| G' at 25° C., MPa | 9.56 | 5.51 | 4.31 | 3.61 |
| δ(ΔG') (kPa) | 1671 | 644 | 741 | 351 |
| $ML_4$ of Masterbatch @ 130° C. | 125.1 | 85.95 | 87.18 | 76.89 |
| $ML_4$ of Remill @ 130° C. | 81.71 | 70.46 | 74.46 | 67.45 |
| $ML_4$ of Final @ 130° C. | 68.85 | 59.5 | 61.55 | 58.84 |
| $t_5$ (seconds) | 1158 | 1379 | 1291 | 1250 |
| Ring tear @ 171° C. | | | | |
| Strength (kN/m) | 8.5 | 10.96 | 12.04 | 11.69 |
| Elongation at break, % | 126 | 194 | 229 | 234 |
| Ring tensile @ 25° C. | | | | |
| M50, MPa | 1.29 | 0.98 | 1.01 | 0.96 |
| M300, MPa | 10.12 | 7.49 | 6.49 | 7.59 |
| Tb, MPa | 15.73 | 13.55 | 15.52 | 13.67 |
| Elongation at break (%) | 411 | 442 | 532 | 432 |
| Toughness, MPa | 27.33 | 24.31 | 33.76 | 23.32 |
| Stanley London Index | 56 | 57 | 61 | 61 |

TABLE 15-continued

Example 22: Test Data

| Property | Comparison Stock 3: S2 silane (phr) | Comparison Stock 4: OTES & Mercapto-silane (phr) | Stock 6: AMS & Mercapto-silane (phr) | Stock 7: AMS & Mercapto-silane/ Imidazole (phr) |
|---|---|---|---|---|
| Max. EtOH % possible from hydrolysis | 0.753 | 0.781 | 0.0784 | 0.0784 |
| Total EtOH % evolved, post mix processing | 0.667 | 0.666 | <0.001% | 0.005% |

As illustrated by the test data presented in Table 15, rubber stocks containing AMS and an added silica-bound mercaptosilane that contained substantially no trialkoxysilane had lower values of −20° C. G' and tan δ at 50° C. than the comparison stock containing a disulfane silica coupling agent and the comparison stocks containing the mercaptosilane in addition to OTES. The addition of the imidazole catalyst to the AMS stock again further improved the physical properties. Therefore, the use of rubber stocks containing AMS and a silica coupling agent or stocks containing AMS, the silica coupling agent, and a catalyst for the alkoxysilane-silica reaction, will produce pneumatic tires having improved silica dispersion and wet and snow traction, lower rolling resistance and decreased hysteresis. Moreover, the total amount of alcohol evolved during compounding and further processing was negligible.

Example 23

Evaluation of AMS and a Guanidine Catalyst in Silica-Filled Rubbers

The AMS prepared in Example 2 (2L) was evaluated in compounding a silica and carbon black-containing rubber according to the method described in Example 15. The catalyst for the AMS-silica reaction was diphenylguanidine (DPG). It is known that guanidines, such as diphenylguanidine (DPG), can be used as a secondary accelerator with a primary accelerator (e.g., a sulfenamide, a thiazole, and the like) and sulfur in the curing stage of rubber. Without being bound by theory, it is believed that in the curing stage, the strongly basic guanidines bind to acid sites remaining on the silica surfaces to prevent binding of zinc, primary accelerators, and other curatives to the silica, in order to allow the sulfur-polymer crosslinking reaction to occur. Thus, guanidines used as secondary accelerators are added, with other curatives and sulfur, in the final stage of mixing at a temperature below the vulcanization temperature, typically not exceeding 120° C., after the major portion of the alkoxysilane-silica reaction has already occurred. In contrast, in the present invention, strong organic bases, such as guanidines, act as catalysts for the AMS-silica reaction in the first, high temperature mixing stage, in the absence of cure agents and added sulfur.

Four rubber stocks were compounded with silica and carbon black, according to the formulations illustrated in Table 16. Comparison stock 5 contained a disulfane silica coupling agent and DPG was added in the final batch as a secondary accelerator. Stock 8 contained AMS from example 2L and DPG was added in the final batch as a secondary

TABLE 16

Example 23: Rubber Compounds

| Ingredient | Comparison Stock 5: S2 Silane (phr) | Stock 8: AMS (Ex 2L) DPG in Final Batch (phr) | Stock 9: AMS DPG in Master Batch and in Final Batch (phr) | Stock 10: AMS DPG in Master Batch only (phr) |
|---|---|---|---|---|
| Master Batch | | | | |
| Solution styrene-butadiene rubber[1] | 100 | 100 | 100 | 100 |
| Precipitated Silica | 30 | 30 | 30 | 30 |
| Carbon Black | 35 | 35 | 35 | 35 |
| Naphthenic Oil | 15 | 12.5 | 12.5 | 12.5 |
| Disulfane silica coupling agent[2] | 2.64 | 0 | 0 | 0 |
| AMS from example 2L | 0 | 2.2 | 2.2 | 2.2 |
| Diphenyl guanidine | 0 | 0 | 0.5 | 0.5 |
| Wax | 1.0 | 1.0 | 1.0 | 1.0 |
| Stearic acid | 1.5 | 1.5 | 1.5 | 1.5 |
| Antioxidant[3] | 0.95 | 0.95 | 0.95 | 0.95 |
| (Drop Temp) | 154° C. | 165° C. | 165° C. | 165° C. |
| Remill | | | | |
| (Drop Temp) Final | 146° C. | 160° C. | 160° C. | 160° C. |
| Sulfur | 1.56 | 1.78 | 1.78 | 1.78 |
| Zinc Oxide | 2.5 | 2.5 | 2.5 | 2.5 |
| Accelerator (CBS)[4] | 1.5 | 1.5 | 1.5 | 1.5 |
| Diphenyl guanidine | 0.5 | 0.5 | 0.5 | 0 |
| PVI | 0.25 | 0.25 | 0.25 | 0.25 |
| (Drop Temp) | 110° C. | 110° C. | 110° C. | 110° C. |

[1] SSBR (23.5% styrene, $T_g$ = −36° C., $ML_4$ = 58)
[2] S2 silane, Silquest A1589 from OSi Specialties
[3] N-(1,3-dimethylbutyl)-N'-phenyl-p-phenylenediamine (6PPD)
[4] N-cyclohexyl-2-benzothiazole sulfenamide (CBS)

accelerator. Stock 9 contained DPG as a catalyst in the master batch, and also contained DPG added in the final batch as a secondary accelerator. Stock 10 contained AMS and DPG in the master batch as a catalyst; however this stock did not contain any added DPG in the final batch.

The Mooney viscosity and curing properties of each of the stocks were evaluated before and during annealing at 171° C. for 15 minutes. The results are illustrated in Table 17.

The green stocks were characterized as to Mooney viscosity ($ML_4$). The Mooney viscosity measurement was conducted at 130° C. using a large rotor, and was recorded as the torque when rotor had rotated for 4 minutes. The stocks were preheated at 130° C. for 1 minute before the rotor was started. The $t_5$ is the time required to increase 5 Mooney units during the Mooney scorch measurement. It is used as an index to predict how fast the compound viscosity will rise during processes such as extrusion. The Monsanto Rheometer MD2000 was used to characterize the stock curing process with conditions of a frequency of 1.67 Hz and a strain of 7% at 160° C. The $t_{s2}$, $t_{10}$ and $t_{90}$, the times at which the torque rises to 2%, 10% and 90%, respectively, of the total torque increase during the curing process, were thus obtained. These times are used to predict how quickly the viscosity builds up ($t_{s2}$, $t_{10}$) and the curing rate ($t_{90}$) during the curing process.

TABLE 17

Example 23: The green stock Mooney viscosity and cure characteristics

| Stock Number | $ML_4$ at 130° C. | $t_5$ scorch @ 130° C. (seconds) | $t_{s2}$ @ 160° C. (min) | $t_{10}$ @ 160° C. (min) | $t_{90}$ @ 160° C. (min) |
|---|---|---|---|---|---|
| Comparison Stock 5: S2 Silane | 68 | 1454 | 4.91 | 4.91 | 15.73 |
| Stock 8: AMS, DPG in final batch | 71.01 | 1206 | 3.51 | 3.96 | 12.91 |
| Stock 9: AMS, DPG in master batch and final batch | 67 | 1074 | 3.56 | 3.91 | 9.1 |
| Stock 10: AMS, DPG in master batch only | 71 | 1292 | 4.63 | 3.97 | 16.88 |

The results of the Mooney and curing characteristics indicate that adding the DPG compound in the master batch as a catalyst for the AMS-silica reaction, and also in the final batch as a secondary accelerator, as in stock 9, provides an improvement in the Mooney viscosity of the green stock, and also improves the $t_{90}$, compared to the stocks containing AMS or disulfane alone in the master batch.

The dynamic viscoelastic mechanical properties of the four stocks were obtained from temperature sweep experiments conducted with a frequency of 31.4 rad/sec using 0.5% strain for temperatures ranging from –100° C. to –20° C. and a 2% strain for temperatures ranging from –20° C. to 100° C. The results are illustrated in Table 18.

TABLE 18

Example 23: The Viscoelastic properties measured by temperature sweep

| Stock Number | G' @ –20° C. (MPa) | tan δ @ 0° C. | tan δ @ 50° C. |
|---|---|---|---|
| Comparison Stock 5: S2 Silane | 31.58 | 0.3144 | 0.1969 |
| Stock 8: AMS, DPG in final batch | 30.66 | 0.3405 | 0.1919 |
| Stock 3: AMS, DPG in master batch and final batch | 31.59 | 0.3541 | 0.1794 |

TABLE 18-continued

Example 23: The Viscoelastic properties measured by temperature sweep

| Stock Number | G' @ –20° C. (MPa) | tan δ @ 0° C. | tan δ @ 50° C. |
|---|---|---|---|
| Stock 4: AMS, DPG in master batch only | 28.88 | 0.3411 | 0.1828 |

Stocks 9 and 10, containing DPG added as a catalyst in the master batch, have lower values of –20° C. G' and 50° C. tan δ, with approximately equivalent values of 0° C. tan δ. These properties are useful in tread compounds because the value of 0° C. tan δ is used to predict the wet traction of the tire tread, the 50° C. tan δ is a predictor of the rolling resistance, and the G' at –20° C. is used to predict snow traction. According to the above results, tires having treads containing the rubber stocks 9 or 10 (DPG in the master batch) are predicted to have better wet and snow traction, and lower rolling resistance, compared to the comparison stocks.

Example 24

Evaluation of Co-AMS-Blocked-Mercapto Octyl Compounds and an Alkyl Tin Catalyst in Silica-Filled Rubbers The product obtained in Example 8, octyl-co-octanoyl blocked mercapto octyl AMS (co-AMS-Oct-Mer), was compounded in rubber stocks. In this example, the use of a catalyst that is a divalent tin compound, tin 2-ethylhexanoate $Sn(EHA)_2$ that promotes the reaction between the alkoxy-modified silsesquioxane and the silica filler, was also evaluated. The ingredients of the rubber compounds, as well as the drop temperatures for the master batch, remill and final stages are listed in Table 19. For comparison purposes, the Stock 1 rubber does not contain any $Sn(EHA)_2$, the Stock 2 rubber contains 0.5 phr $Sn(EHA)_2$, and the Stock 3 rubber contains 1.0 phr $Sn(EHA)_2$. All of the compounded final stocks were sheeted and subsequently annealed at 171° C. for 15 minutes.

TABLE 19

Example 24: Rubber Compositions

| Ingredient | Stock 11 0 phr $Sn(EHA)_2$ | Stock 12 0.5 phr $Sn(EHA)_2$ | Stock 13 1.0 phr $Sn(EHA)_2$ |
|---|---|---|---|
| Master Batch 1 | | | |
| Styrene-butadiene Rubber[1] | 85 | 85 | 85 |
| Butadiene Rubber[2] | 15 | 15 | 15 |
| Precipitated Silica | 33.7 | 33.7 | 33.7 |
| Carbon Black | 20 | 20 | 20 |
| Disulfane silica coupling agent[3] | 0.95 | 0.95 | 0.95 |
| Co-AMS-blocked-mercapto octyl (Ex 8) | 1.47 | 1.47 | 1.47 |
| SMO[4] | 1.33 | 1.33 | 1.33 |
| Sn (EHA) | 0 | 0.5 | 1.0 |
| Wax | 1.0 | 1.0 | 1.0 |
| (Drop Temp) | 165° C. | 165° C. | 165° C. |

TABLE 19-continued

Example 24: Rubber Compositions

| Ingredient | Stock 11 0 phr Sn(EHA)$_2$ | Stock 12 0.5 phr Sn(EHA)$_2$ | Stock 13 1.0 phr Sn(EHA)$_2$ |
|---|---|---|---|
| Master Batch 2 | | | |
| Precipitated Silica | 22.3 | 22.3 | 22.3 |
| Co-AMS-blocked-mercapto octyl (Ex 8) | 0.73 | 0.73 | 0.73 |
| SMO[4] | 0.66 | 0.66 | 0.66 |
| (Drop Temp) | 165° C. | 165° C. | 165° C. |
| Remill | | | |
| (Drop Temp) | 160° C. | 160° C. | 160° C. |
| Final | | | |
| MBTS[5] | 0.8 | 0.8 | 0.8 |
| Zinc Oxide | 2.5 | 2.5 | 2.5 |
| TBBS[6] | 0.8 | 0.8 | 0.8 |
| Diphenyl guanidine | 1.0 | 1.0 | 1.0 |
| (Drop Temp) | 110° C. | 110° C. | 110° C. |

[1]SBR (25% styrene, T$_g$ −45° C., ML$_4$ 58, 37.5 phr extended aromatic oil)
[2]BR (1% vinyl, Tg −110° C., 8 phr aromatic oil)
[3]N-(1,3-dimethylbutyl)-N'-phenyl-p-phenylenediamine (6PPD)
[4]Sulfated methyl oleate Monosodium salt (SMO)
[5]2,2'-dithiobis(benzothiazole) (MBTS)
[6]N-tert-butyl-2-benzothiazyl sulfenamide (TBBS)

The Mooney viscosity and the curing properties (t$_{s2}$ and t$_{90}$) of each of the stocks were evaluated. The results are listed in Table 20. The green stocks were characterized as to Mooney viscosity (ML$_4$) and the Monsanto Rheometer MD2000 was used to characterize the stock curing process using the methods discussed above in Example 23. The t$_{s2}$ time is used to predict how quickly viscosity builds up and the t$_{90}$ time indicates the curing rate.

TABLE 20

Example 24: Green Stock Mooney Viscosity and Cure Characteristics

| Stock Number | ML$_4$ at 130° C. | t$_{s2}$ @ 160° C. (min) | t$_{90}$ @ 160° C. (min) |
|---|---|---|---|
| Stock 11 0 phr Sn(EHA)$_2$ | 73.16 | 0.199 | 25.89 |
| Stock 12 0.5 phr Sn(EHA)$_2$ | 77.38 | 0.18 | 25.66 |
| Stock 13 1.0 phr Sn(EHA)$_2$ | 76.08 | 0.178 | 26.62 |

The results of the Mooney and curing characteristics indicate that adding Sn(EHA)$_2$, provides an improvement in the Mooney viscosity of the green stock, but does not significantly alter the t$_{s2}$ or t$_{90}$ times.

The dynamic viscoelastic mechanical properties of the three stocks were obtained from temperature sweep experiments (TS) conducted with a frequency of 31.4 rad/sec using 0.5% strain for temperatures ranging from −100° C. to −20° C. and a 2% strain for temperatures ranging from −20° C. to 100° C. The tan δ at 50° C. for a strain sweep experiment (SS) was also obtained using a frequency of 3.14 rad/sec at 50° C. with strain sweeping from 0.25% to 14.75%. The results are listed in Table 21.

TABLE 21

Example 24: Viscoelastic Properties

| Stock Number | G' @ −20° C. (MPa) TS | tan δ @ 0° C. TS | tan δ @ 50° C. TS | tan δ @ 50° C. SS |
|---|---|---|---|---|
| Stock 11 0 phr Sn(EHA)$_2$ | 25.18 | 0.2632 | 0.1966 | 0.2029 |
| Stock 12 0.5 phr Sn(EHA)$_2$ | 22.26 | 0.2761 | 0.2029 | 0.1966 |
| Stock 13 1.0 phr Sn(EHA)$_2$ | 22.89 | 0.2832 | 0.2134 | 0.2089 |

Stocks 12 and 13, which contain Sn(EHA)$_2$, have lower values of G' @ −20° C., higher tan δ @ 0° C. values, and similar values of tan δ @ 50° C. as compared to Stock 11. The trends in the temperature sweep (TS) test values provide indications of specific tire performance aspects: G' @ −20° C. values are used to predict snow traction (a lower value indicates better snow traction); tan δ @ 0° C. values are used to predict wet traction (a higher value indicates better wet traction); and tan δ @ 50° C. values are used to predict rolling resistance. Thus, Stocks 12 and 13 (those compounds containing Sn(EHA)$_2$) are predicted to have better wet and snow traction while maintaining a similar rolling resistance when compared to Stock 11 (no Sn(EHA)$_2$).

The tensile mechanical properties of Stocks 11, 12 and 13 were also measured using the standard procedure described in ASTM-D 412 at 25. Test specimens were nicked round rings with an inside diameter of 44 mm, an outside diameter of 57.5 mm, and a thickness of 2.5 mm. The gauge length used for the tensile testing was 25.4 mm. The tensile mechanical properties measured for Stocks 11, 12 and 13 are listed in Table 22.

TABLE 22

Example 24: Tensile Mechanical Properties

| Stock Number | M50 (MPa) | M300 (MPa) | Tb (MPa) | Eb (%) | Toughness (MPa) |
|---|---|---|---|---|---|
| Stock 11 0 phr Sn(EHA)$_2$ | 1.13 | 6.93 | 13.73 | 482 | 27.94 |
| Stock 12 0.5 phr Sn(EHA)$_2$ | 1.13 | 6.48 | 15.31 | 542 | 34.78 |
| Stock 13 1.0 phr Sn(EHA)$_2$ | 1.09 | 6.08 | 15.68 | 570 | 37.15 |

Each of the tensile mechanical properties listed in Table 24 improved with the addition of Sn(EHA)$_2$ for Stocks 12 and 13.

Overall the results of Example 24 indicate that the processability, viscoelastic properties, and mechanical properties of Stocks 2 and 3 were improved by the addition of Sn(EHA)$_2$.

Example 25

Evaluation of Co-AMS-Block-Mercapto Octyl Compounds and an Alkyl Zirconium Catalyst in Silica-Filled Rubbers The product obtained in Example 8, octyl-co-octanoyl blocked mercaptopropyl AMS (co-AMS-Oct-Mer), was compounded in rubber stocks. In this example, the use of a catalyst that is a divalent zirconium compound, zirconium 2-ethylhexanoate Zr(EHA)$_2$ that promotes the reaction between the alkoxy-modified silsesquioxane and the silica filler, was also evaluated. The ingredients of the rubber compounds, as well as the drop temperatures for the master batch, remill and final stages are listed in Table 25. For comparison purposes, the Stock 11 rubber does not contain any Zr(EHA)$_2$, the Stock 14 rubber contains 0.5 phr Zr(EHA)$_2$, and the Stock 15 rubber contains 1.0 phr Zr(EHA)$_2$. All of the compounded final stocks were sheeted and subsequently annealed at 171° C. for 15 minutes.

TABLE 25

Example 25: Rubber Compositions

| Ingredient | Stock 11 0 phr Zr(EHA)$_2$ | Stock 14 0.5 phr Zr(EHA)$_2$ | Stock 15 1.0 phr Zr(EHA)$_2$ |
|---|---|---|---|
| Master Batch 1 | | | |
| Styrene-butadiene Rubber[1] | 85 | 85 | 85 |
| Butadiene Rubber[2] | 15 | 15 | 15 |
| Precipitated Silica | 33.7 | 33.7 | 33.7 |
| Carbon Black | 20 | 20 | 20 |
| Disulfane silica coupling agent[3] | 0.95 | 0.95 | 0.95 |
| Co-AMS-blocked-mercapto octyl (Ex 8) | 1.47 | 1.47 | 1.47 |
| SMO[4] | 1.33 | 1.33 | 1.33 |
| Zr(EHA)$_2$ | 0 | 0.5 | 1.0 |
| Wax | 1.0 | 1.0 | 1.0 |
| (Drop Temp) | 165° C. | 165° C. | 165° C. |
| Master Batch 2 | | | |
| Precipitated Silica | 22.3 | 22.3 | 22.3 |
| Co-AMS-blocked-mercapto octyl (Ex 8) | 0.73 | 0.73 | 0.73 |
| SMO[4] | 0.66 | 0.66 | 0.66 |
| (Drop Temp) | 165° C. | 165° C. | 165° C. |
| Remill | | | |
| (Drop Temp) | 160° C. | 160° C. | 160° C. |
| Final | | | |
| MBTS[5] | 0.8 | 0.8 | 0.8 |
| Zinc Oxide | 2.5 | 2.5 | 2.5 |
| TBBS[6] | 0.8 | 0.8 | 0.8 |
| Diphenyl guanidine | 1.0 | 1.0 | 1.0 |
| (Drop Temp) | 110° C. | 110° C. | 110° C. |

[1]SBR (25% styrene, T$_g$ −45° C., ML$_4$ 58, 37.5 phr extended aromatic oil)
[2]BR (1% vinyl, Tg −110° C., 8 phr aromatic oil)
[3]N-(1,3-dimethylbutyl)-N'-phenyl-p-phenylenediamine (6PPD)
[4]Sulfated methyl oleate Monosodium salt (SMO)
[5]2,2'-dithiobis(benzothiazole) (MBTS)
[6]N-tert-butyl-2-benzothiazyl sulfenamide (TBBS)

The Mooney viscosity and the curing properties ($t_5$, $t_{s2}$ and $t_{90}$) of each of the stocks were evaluated. The results are listed in Table 26. The green stocks were characterized as to Mooney viscosity (ML$_4$) and the Monsanto Rheometer MD2000 was used to characterize the stock curing process using the methods discussed above in Example 23. The $t_5$ time is used as an index to predict how fast the compound viscosity will rise during processing, $t_{s2}$ time is used to predict how quickly viscosity builds up and the $t_{90}$ time indicates the curing rate.

TABLE 26

Example 25: Green Stock Mooney Viscosity and Cure Characteristics

| Stock Number | ML$_4$ @ 130° C. | $t_5$ @ 130° C. (sec) | $t_{s2}$ @ 160° C. (min) | $t_{90}$ @ 160° C. (min) |
|---|---|---|---|---|
| Stock 11 0 phr Zr(EHA)$_2$ | 74.17 | 604 | 1.41 | 25.32 |
| Stock 14 0.5 phr Zr(EHA)$_2$ | 77.11 | 688 | 1.45 | 25.71 |
| Stock 15 1.0 phr Zr(EHA)$_2$ | 76.44 | 813 | 1.6 | 25.77 |

The results of the Mooney and curing characteristics indicate that adding Zr(EHA)$_2$, provides an improvement in the Mooney viscosity of the green stock and improves $t_5$, but does not significantly alter the $t_{s2}$ or $t_{90}$ times.

The dynamic viscoelastic mechanical properties of the three stocks were obtained from temperature sweep experiments (TS) conducted with a frequency of 31.4 rad/sec using 0.5% strain for temperatures ranging from −100° C. to −20° C. and a 2% strain for temperatures ranging from −20° C. to 100° C. The tan δ at 0° C. and 50° C. were also obtained for dynamic compression test measurements. The sample geometry for the dynamic compression test measurements was a cylindrical button with a 9.5 mm diameter and a 15.6 mm length. Each sample was compressed under a static load of 1.25 Kg at a frequency of 1 Hz. Then each sample was dynamically compressed and extended and the tan δ values were obtained. The results are listed in Table 27.

TABLE 27

Example 25: Viscoelastic Properties

| Stock Number | G' @ −20° C. TS (MPa) | tan δ @ 0° C. TS | tan δ @ 50° C. TS | tan δ @ 0° C. Compression | tan δ @ 50° C. Compression |
|---|---|---|---|---|---|
| Stock 11 0 phr Zr(EHA)$_2$ | 25.57 | 0.2699 | 0.2008 | 0.2241 | 0.2020 |
| Stock 14 0.5 phr Zr(EHA)$_2$ | 25.3 | 0.2781 | 0.2048 | 0.2592 | 0.2049 |
| Stock 15 1.0 phr Zr(EHA)$_2$ | 22.71 | 0.2782 | 0.2075 | 0.2683 | 0.2087 |

Stocks 14 and 15, which contain $Zr(EHA)_2$, have lower values of G' @ −20° C., higher tan δ @ 0° C. values, and similar values of tan δ @ 50° C. as compared to Stock 11. The trends in the temperature sweep (TS) and compression test values provide indications of specific tire performance aspects: G' @ −20° C. values are used to predict snow traction (a lower value indicates better snow traction); tan δ @ 0° C. values are used to predict wet traction (a higher value indicates better wet traction); and tan δ @ 50° C. values are used to predict rolling resistance. Thus, Stocks 14 and 15 (those compounds containing $Zr(EHA)_2$) are predicted to have better wet and snow traction while maintaining a similar rolling resistance when compared to Stock 11 (no $Zr(EHA)_2$).

The rebound resilience of the rubber compounds was measured using a Zwick rebound resilience tester. In the Zwick tester, a test sample (a round piece with a 38.1 mm diameter and a 19 mm thickness that has been preheated at 50° C. for 30 minutes prior to testing) is subjected to one half-cycle of deformation. Each sample is strained by impacting the test piece with an indentor that is free to rebound after impact. Rebound resilience is defined as the ratio of mechanical energies before and after impact. The rebound resiliencies of Stocks 11, 14 and 15 are listed in Table 28.

TABLE 28

Example 25: Rebound Resilience

| Stock Number | Rebound @ 50° C. |
|---|---|
| Stock 11<br>0 phr $Zr(EHA)_2$ | 48.6 |
| Stock 14<br>0.5 phr $Zr(EHA)_2$ | 48.2 |
| Stock 15<br>1.0 phr $Zr(EHA)_2$ | 48.0 |

The rebound resiliencies measured for Stocks 11, 14 and 15 show that the rebound resiliency is not appreciably changed with the addition of $Zr(EHA)_2$.

The tensile mechanical properties of Stocks 11, 14 and 15 were also measured using the standard procedure described in ASTM-D 412 at 25. Test specimens were nicked round rings with an inside diameter of 44 mm, an outside diameter of 57.5 mm, and a thickness of 2.5 mm. The gauge length used for the tensile testing was 25.4 mm. The tensile mechanical properties measured for Stocks 11, 14 and 15 are listed in Table 29.

TABLE 29

Example 25: Tensile Mechanical Properties

| Stock Number | M50 (MPa) | M300 (MPa) | Tb (MPa) | Eb (%) | Toughness (MPa) |
|---|---|---|---|---|---|
| Stock 11<br>0 phr $Zr(EHA)_2$ | 1.19 | 6.99 | 16.01 | 534 | 36 |
| Stock 14<br>0.5 phr $Zr(EHA)_2$ | 1.18 | 6.73 | 16.35 | 561 | 38.96 |
| Stock 15<br>1.0 phr $Zr(EHA)_2$ | 1.17 | 6.12 | 16.14 | 582 | 39.51 |

Each of the tensile mechanical properties listed in Table 29 improved with the addition of $Zr(EHA)_2$ for Stocks 14 and 15.

Overall the results of Example 25 indicate that the processability, viscoelastic properties, and mechanical properties of Stocks 14 and 15 were improved by the addition of $Zr(EHA)_2$.

Example 26

Evaluation of Co-AMS-Block-Mercapto Propyl Compounds in Silica-Filled Rubbers Using Different Master Batch and Remill Drop Temperatures The product obtained in Example 10, octyl-co-mercaptopropyl. AMS, was compounded in rubber stocks using various drop temperatures during master batch mixing and a first remill mixing. The master batch and first remill drop temperatures for stocks 16, 17, and 18 are listed in Table 30. The ingredients of the rubber compounds, as well as the drop temperatures for the second remill and final stages are listed in Table 31. All of the compounded final stocks were sheeted and subsequently annealed at 171° C. for 15 minutes.

TABLE 30

Example 26: Master Batch and Remill 1 Drop Temperatures for Stocks 16, 17, and 18

| Drop Temperature | Stock 16 | Stock 17 | Stock 18 |
|---|---|---|---|
| Master Batch (° C.) | 145 | 155 | 170 |
| Remill 1 (° C.) | 145 | 155 | 170 |

TABLE 31

Example 26: Basic Rubber Composition

| Ingredient | Stock 2:<br>co-AMS-mercapto<br>propyl-octyl (Ex 10)<br>(phr) |
|---|---|
| Master Batch 1 | |
| Solution styrene-butadiene rubber[1] | 116.88 |
| High-cis butadiene rubber[2] | 15 |
| Precipitated Silica | 37.33 |
| Carbon Black | 20 |
| co-AMS-mercapto propyl-octyl (Ex 10) | 1.57 |
| SMO[3] | 1.33 |
| Wax | 1.0 |
| Antioxidant[4] | 0.95 |
| (Drop Temp) | See Table 30 |
| Remill 1 | |
| Silica | 18.67 |
| co-AMS-mercapto propyl-octyl (Ex 10) | 0.78 |
| SMO[3] | 0.67 |
| (Drop Temp) | See Table 30 |
| Remill 2 | |
| (Drop Temp) | 145° C. |
| Final | |
| Zinc Oxide | 2.5 |
| MBTS[5] | 0.8 |
| TBBS[6] | 0.8 |
| Diphenyl guanidine | 1.0 |
| (Drop Temp) | 110° C. |

[1]SSBR (25% styrene, $T_g$ = −45° C., 37.5 phr extended aromatic oil)
[2]BR (1% vinyl, Tg = −110° C., 8 phr extended aromatic oil)
[3]Sulfated methyl oleate Monosodium salt (SMO)
[4]N-(1,3-dimethylbutyl)-N'-phenyl-p-phenylenediamine (6PPD)
[5]2,2'-dithiobis(benzothiazole) (MBTS)
[6]N-tert-butyl-2-benzothiazyl sulfenamide (TBBS)

The Mooney viscosity and several curing properties ($t_{s2}$ and $t_{90}$) of each of the stocks were evaluated. The results are listed in Table 32. The green stocks were characterized as to Mooney viscosity ($ML_4$) and the Monsanto Rheometer MD2000 was used to characterize the stock curing process using the methods discussed above in Example 23. The $t_{s2}$ time is used to predict how quickly viscosity builds up and the $t_{90}$ time indicates the curing rate.

TABLE 32

Example 26: Green Stock Mooney Viscosity and Cure Characteristics

| Stock Number | $ML_4$ @ 130° C. | $t_{s2}$ @ 160° C. (min) | $t_{90}$ @ 160° C. (min) |
|---|---|---|---|
| Stock 16 | 84.5 | 1.25 | 21.92 |
| Stock 17 | 83.1 | 1.28 | 22.02 |
| Stock 18 | 81.3 | 1.26 | 20.85 |

The results of the Mooney and curing characteristics indicate that increasing the drop temperatures of the master batch and remill 1 mixing steps provides an improvement in the Mooney viscosity of the green stock and decreases $t_{90}$, but does not significantly alter the $t_{s2}$ time.

The dynamic viscoelastic mechanical properties of the three stocks were obtained from temperature sweep experiments (TS) conducted with a frequency of 31.4 rad/sec using 0.5% strain for temperatures ranging from −100° C. to −20° C. and a 2% strain for temperatures ranging from −20° C. to 100° C. The tan δ at 0° C. and 50° C. were also obtained for dynamic compression test measurements. The sample geometry for the dynamic compression test measurements was a cylindrical button with a 9.5 mm diameter and a 15.6 mm length. Each sample was compressed under a static load of 1.25 kg at a frequency of 1 Hz. Then each sample was dynamically compressed and extended and the tan δ values were obtained. The results are listed in Table 33.

TABLE 33

Example 26: Viscoelastic Properties

| Stock Number | G' @ −20° C. TS (MPa) | tan δ @ 0° C. TS | tan δ @ 50° C. TS | tan δ @ 0° C. Compression | tan δ @ 50° C. Compression |
|---|---|---|---|---|---|
| Stock 16 | 21.89 | 0.2513 | 0.1718 | 0.2289 | 0.1864 |
| Stock 17 | 21.32 | 0.2617 | 0.1796 | 0.2348 | 0.1853 |
| Stock 18 | 19.88 | 0.2649 | 0.1769 | 0.2598 | 0.1749 |

Stocks 17 and 18, which had elevated drop temperatures, have lower values of G' @ −20° C., higher tan δ @ 0° C. values, and similar values of tan δ @ 50° C. as compared to Stock 16. The trends in the temperature sweep (TS) and compression test values provide indications of specific tire performance aspects: G' @ −20° C. values are used to predict snow traction (a lower value indicates better snow traction); tan δ @ 0° C. values are used to predict wet traction (a higher value indicates better wet traction); and tan δ @ 50° C. values are used to predict rolling resistance. Thus, Stocks 17 and 18 (those compounds produced using elevated drop temperatures) are predicted to have better wet and snow traction while maintaining a similar rolling resistance when compared to Stock 16.

The rebound resilience of the rubber compounds was measured using a Zwick rebound resilience tester. In the Zwick tester, a test sample (a round piece with a 38.1 mm diameter and a 19 mm thickness that has been preheated at 50° C. for 30 minutes prior to testing) is subjected to one half-cycle of deformation. Each sample is strained by impacting the test piece with an indentor that is free to rebound after impact. Rebound resilience is defined as the ratio of mechanical energies before and after impact. The rebound resiliencies of Stocks 11, 14 and 15 are listed in Table 34.

TABLE 34

Example 26: Rebound Resilience

| Stock Number | Rebound @ 50° C. |
|---|---|
| Stock 16 | 52 |
| Stock 17 | 52 |
| Stock 18 | 53 |

The rebound resiliencies measured for Stocks 16, 17 and 18 show that the rebound resiliency is not appreciably changed with the elevated drop temperatures. These rebound resilience values support the tan δ @ 50° C. values (indicating similar rolling resistance).

The bound rubber content and abrasion (wear) resistance were also measured for Stocks 16, 17 and 18. The bound rubber content is a measure of the percent of polymer bound to filler particles in a rubber stock. The amount of bound rubber is measured by immersing a rubber sample into a solvent (in this case toluene) for several days (in this case three days). Any soluble rubber in the sample, i.e., rubber not bound to filler particles, is extracted from the rubber sample by the solvent. When the solvent exposure period is complete the excess solvent is drained off and the sample is dried first in air then in a drying oven (at a temperature of 100° C. in this case). The amount of rubber remaining with the filler is the bound rubber. The bound rubber content is calculated by the following formula:

$$\% \; BoundRubber = \frac{100(W_d - F)}{R}$$

Where $W_d$ is the weight of the dried sample, F is the weight of filler in the sample (same as the original amount), and R is the weight of the original sample. As shown in Table 35, the % Bound Rubber increases slightly for Stock 18 which had the highest drop temperatures.

The abrasion (wear) resistance for each stock was evaluated by weighting the amount of wear using the Lambuorn test. Test samples comprise circular donuts with an inner diameter of about 22.9 mm, an outer diameter of about 48.3 mm, and a thickness of about 5 mm. The test samples were placed on an axle and run as a slip ratio of 65% against a driven abrasive surface for a period of time. The slope of weight loss (wearing rate) was measured versus time. The wearing index was obtained by dividing the wearing rate of a control sample by the wearing rate of the tested sample. Samples with higher wear indices have better wear resistance. As shown in Table 35, Stocks 17 and 18 have higher wear indices than Stock 16.

TABLE 35

Example 26: Bound Rubber and Abrasion Resistance

| Stock Number | % Bound Rubber | Abrasion Resistance Index |
|---|---|---|
| Stock 16 | 49 | 103 |
| Stock 17 | 49 | 105 |
| Stock 18 | 51 | 107 |

The tensile mechanical properties of Stocks 16, 17 and 18 were further measured using the standard procedure described in ASTM-D 412 at 25. Test specimens were nicked round rings with an inside diameter of 44 mm, an outside diameter of 57.5 mm, and a thickness of 2.5 mm. The gauge length used for the tensile testing was 25.4 mm. The tensile mechanical properties measured for Stocks 16, 17 and 18 are listed in Table 36.

TABLE 36

Example 26: Tensile Mechanical Properties

| Stock Number | M50 (MPa) | M300 (MPa) | Tb (MPa) | Eb (%) | Toughness (MPa) |
|---|---|---|---|---|---|
| Stock 16 | 1.13 | 8.75 | 18.62 | 508 | 39.64 |
| Stock 17 | 1.07 | 8.33 | 17.47 | 500 | 36.11 |
| Stock 18 | 1.01 | 7.65 | 17.6 | 527 | 38.09 |

Each of the tensile mechanical properties listed in Table 36 improved or did not appreciably change with the increased drop temperatures.

While the invention has been described herein with reference to the preferred embodiments, it is to be understood that it is not intended to limit the invention to the specific forms disclosed. On the contrary, it is intended that the invention cover all modifications and alternative forms falling within the scope of the appended claims.

We claim:

1. An alkoxy-modified silsesquioxane comprising one or more compounds selected from the group consisting of alkoxy-modified silsesquioxanes having the formula

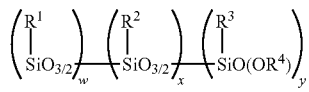

and mixtures thereof, wherein w, x and y represent mole fractions, y does not equal zero, either w or x but not both can be zero, and w+x+y=1.00,
wherein $R^1$, $R^2$ and $R^3$ are selected from the group consisting of (i) H or an alkyl groups having one to about 20 carbon atoms, (ii) cycloalkyl groups having 3 to about 20 carbon atoms, (iii) alkylaryl groups having 7 to about 20 carbon atoms, and (iv) $R^5X$, wherein X is selected from the group consisting of Cl, Br, SH, $S_aR^6$, $NR^6_2$, $OR^6$, $CO_2H$, $CO_2R^6$, $SCOR^6$, OH, olefins, epoxides, amino groups, vinyl groups, acrylates and methacrylates, wherein a=1 to about 8, $R^5$ is selected from the group consisting of alkylene groups having one to about 20 carbon atoms, cycloalkylene groups having 3 to about 20 carbon atoms, and $R^4$ and $R^6$ are selected from the group consisting of alkyl groups having one to about 5 carbon atoms, cycloalkyl groups having 3 to about 20 carbon atoms, and alkylaryl groups having 7 to about 20 carbon atoms,
wherein the alkoxy-modified silsesquioxanes consist essentially of a mixture of alkoxy-modified silsesquioxanes having an open structure with a reactive alkoxysilyl group, and are essentially free of closed caged polyhedral organosilsesquioxanes,
and wherein the mixture of alkoxy-modified silsesquioxanes liberates about 0.05% to about 10% by weight alcohol when treated by substantially total acid hydrolysis.

2. An alkoxy-modified silsesquioxane as defined in claim 1, wherein when neither w nor x is zero, the ratio of the w mole fraction to the (w+x) mole fraction can range from about 0.01 to about 0.50.

3. An alkoxy-modified silsesquioxane as defined in claim 1, wherein the mixture of alkoxy-modified silsesquioxanes liberates about 0.5% to about 8% by weight alcohol when treated by substantially total acid hydrolysis.

4. An alkoxy-modified silsesquioxane as defined in claim 1, wherein the mixture of alkoxy-modified silsesquioxanes liberates about 1% to about 6% by weight alcohol when treated by substantially total acid hydrolysis.

5. An alkoxy-modified silsesquioxane as defined in claim 1, wherein at least one of the $R^1$, $R^2$ and $R^3$ groups of the alkoxy-modified silsesquioxane is a group that can bind to an elastomer.

6. An alkoxy-modified silsesquioxane as defined in claim 5, wherein the at least one of the $R^1$, $R^2$ and $R^3$ groups is selected from the group consisting of a mercaptoalkyl group, a blocked mercaptoalkyl group and an organo group containing a chain of about 2 to about 8 sulfur atoms.

7. An alkoxy-modified silsesquioxane as defined in claim 1, wherein at least one of the one or more compounds comprises an alkyl alkoxy-modified silsesquioxane.

8. An alkoxy-modified silsesquioxane as defined in claim 7, wherein the alkyl alkoxy-modified silsesquioxane is selected from the group consisting of octyl alkoxy-modified silsesquioxanes, 2-ethylhexyl alkoxy-modified silsesquioxanes, phenyl alkoxy-modified silsesquioxanes, 3-chloropropyl alkoxy-modified silsesquioxanes, 3-mercaptopropyl alkoxy-modified silsesquioxanes, thioacylpropyl alkoxy-modified silsesquioxanes, thiooctanoylpropyl alkoxy-modified silsesquioxanes, and mixtures thereof.

9. An alkoxy-modified silsesquioxane as defined in claim 8, wherein the alkyl alkoxy-modified silsesquioxane comprises an alkyl-co-mercapto alkoxy-modified silsesquioxane.

10. A method for making a mixture of alkoxy-modified silsesquioxanes comprising:
(a) combining as a reaction mixture:
(i) water;
(ii) alcohol;
(iii) a R-trialkoxysilane, a R-trichlorosilane, or a mixture thereof,
wherein R comprises a group bonded to the silicon atom and is independently selected from the group consisting of $R^1$, $R^2$ and $R^3$, wherein $R^1$, $R^2$ and $R^3$ are selected from the group consisting of (1) H or an alkyl groups having one to about 20 carbon atoms, (2) cycloalkyl groups having 3 to about 20 carbon atoms, (3) alkylaryl groups having 7 to about 20 carbon atoms, and (4) $R^5X$, wherein X is selected from the group consisting of Cl, Br, SH, $S_aR^6$, $NR^6_2$, $OR^6$, $CO_2H$, $CO_2R^6$, $SCOR^6$, OH, olefins, epoxides, amino groups, vinyl groups, acrylates and methacrylates, wherein a=1 to about 8, $R^5$ is selected from the group consisting of alkylene groups having one to about 20 carbon atoms, cycloalkylene groups having 3 to about 20 carbon atoms, $R^4$ and $R^6$ are selected from the group consisting of alkyl groups having one to about 5 carbon atoms, cycloalkyl groups having 3 to about 20 carbon atoms, and alkylaryl groups having 7 to about 20 carbon atoms; and
(iv) a hydrolysis and condensation catalyst;
(b) allowing the reaction mixture to react for about 0.5 hours to about 200 hours; and
(c) recovering the alkoxy-modified silsesquioxane,
wherein the mixture of alkoxy-modified silsesquioxanes consists essentially of alkoxy-modified silsesquioxanes having an open structure with a reactive alkoxysilyl group, and is essentially free of closed caged polyhedral organosilsesquioxanes, and wherein the mixture of alkoxy-modified silsesquioxanes liberates about 0.05% to about 10% by weight alcohol when treated by substantially total acid hydrolysis.

11. A method as defined in claim 10, wherein the alcohol in the reaction mixture comprises ethanol or methanol.

12. A method as defined in claim 10, wherein the alkyltrialkoxysilane is selected from the group consisting of octyltriethoxysilane, octyltrimethoxysilane, cyclohexyltriethoxysilane, isobutyltriethoxysilane, ethyltrimethoxysilane, cyclohexyltributoxysilane, methyl-triethoxysilane, propyltriethoxysilane, hexyltriethoxysilane, heptyltriethoxysilane, nonyl-triethoxysilane, decyltriethoxysilane, n-dodecyltrialkoxysilane, octadecyltriethoxysilane, methyltrimethoxysilane, propyltrimethoxysilane, hexyltrimethoxysilane, heptyltrimethoxysilane, nonyltrimethoxysilane, octadecyltrimethoxysilane, 2-ethylhexyl-triethoxysilane, and mixtures thereof.

13. A method as defined in claim 10, wherein the alkyltrichlorosilane is selected from the group consisting of octyltrichlorosilane, cyclohexyltrichlorosilane, isobutyltrichlorosilane, ethyltrichlorosilane, methyltrichlorosilane, propyltrichlorosilane, hexyltrichlorosilane, heptyltrichlorosilane, nonyltrichlorosilane, octadecyltrichlorosilane, and mixtures thereof.

14. A method as defined in claim 10, wherein the hydrolysis and condensation catalyst is selected from the group consisting of hydrochloric acid, sulfuric acid, phosphoric acid, sodium hydroxide, potassium hydroxide, lithium hydroxide, (1,8-diazabicyclo [5.4.0]undec-7-ene), imidazoles, guanidines, and mixtures thereof.

15. A method as defined in claim 10, wherein the reaction mixture is allowed to react for about 0.75 hours to about 120 hours.

16. A method as defined in claim 10, wherein the reaction mixture is allowed to react for about one hour to about 72 hours.

17. A method as defined in claim 10, wherein the alkoxy-modified silsesquioxane is recovered by phase separation.

18. A method as defined in claim 10, wherein the R-trialkoxysilane comprises an alkyltrialkoxysilane.

19. A method as defined in claim 10, wherein the R-trichlorosilane comprises an alkyltrichlorosilane.

20. A method as defined in claim 10, wherein step (c) further comprises the substep of reacting an alkoxy-modified silsesquioxane comprising the S atom of a mercapto group, when X is SH, with a reagent that chemically reacts with the S atom to add a $COR^6$ group to the alkoxy-modified silsesquioxane.

21. A vulcanizable rubber compound comprising
(a) an elastomer;
(b) a reinforcing filler comprising silica or a mixture thereof with carbon black;
(c) a silica dispersing aid comprising an alkoxy-modified silsesquioxane that comprises one or more compounds selected from the group consisting of alkoxy-modified silsesquioxanes having the formula

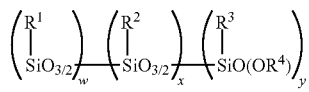

and mixtures thereof, wherein w, x and y represent mole fractions, y does not equal zero, either w or x but not both can be zero, and w+x+y=1.00, wherein $R^1$, $R^2$ and $R^3$ are selected from the group consisting of (i) H or an alkyl groups having one to about 20 carbon atoms, (ii) cycloalkyl groups having 3 to about 20 carbon atoms, (iii) alkylaryl groups having 7 to about 20 carbon atoms, and (iv) $R^5X$, wherein X is selected from the group consisting of Cl, Br, SH, $S_aR^6$, $NR^6_2$, $OR^6$, $CO_2H$, $CO_2R^6$, $SCOR^6$, OH, olefins, epoxides, amino groups, vinyl groups, acrylates and methacrylates, wherein a=1 to about 8, $R^5$ is selected from the group consisting of alkylene groups having one to about 20 carbon atoms, cycloalkylene groups having 3 to about 20 carbon atoms, and $R^4$ and $R^6$ are selected from the group consisting of alkyl groups having one to about 5 carbon atoms, cycloalkyl groups having 3 to about 20 carbon atoms, and alkylaryl groups having 7 to about 20 carbon atoms, wherein the alkoxy-modified silsesquioxanes consist essentially of a mixture of alkoxy-modified silsesquioxanes having an open structure with a reactive alkoxysilyl group, and essentially free of closed caged polyhedral organosilsesquioxanes, and wherein the alkoxy-modified silsesquioxanes liberate about 0.05% to about 10% by weight alcohol when treated by substantially total acid hydrolysis; and
(d) a cure agent.

22. A rubber compound as defined in claim 21, wherein the silica is present in an amount of about 15 phr to about 120 phr.

23. A rubber compound as defined in claim 21, wherein the alkoxy-modified silsesquioxane is present in an amount of about 0.1% to about 20% by weight based on the silica.

24. A rubber compound as defined in claim 21, wherein the mixture of alkoxy-modified silsesquioxanes liberates about 0.1% to about 8% by weight alcohol when treated by substantially total acid hydrolysis.

25. A rubber compound as defined in claim 21, wherein the mixture of alkoxy-modified silsesquioxanes liberates about 1% to about 6% by weight alcohol when treated by substantially total acid hydrolysis.

26. A rubber compound as defined in claim 21, wherein an amount of alcohol released as VOC during compounding and further processing is zero to about 0.1% by weight of the rubber compound.

27. A rubber compound as defined in claim 21, wherein an amount of alcohol released as VOC during compounding and further processing is zero to about 0.05% by weight of the rubber compound.

28. A rubber compound as defined in claim 21 further comprising a sulfur containing coupling agent.

29. A rubber compound as defined in claim 28, wherein the sulfur containing coupling agent is present in an amount of about 0.05% to about 3% based on the amount of silica present.

30. A rubber compound as defined in claim 29, wherein the sulfur containing coupling agent is selected from the group consisting of mercaptoalkyltrialkoxy silanes, blocked mercaptoalkyltrialkoxy silanes, mercaptoalkylsilanes bound to silica, blocked mercaptoalkylsilanes bound to silica, bis(trialkoxysilylorgano) tetrasulfides or disulfides, and mixtures thereof.

31. A rubber compound as defined in claim 29, wherein the sulfur containing coupling agent is a mercaptoalkylsilane bound to silica with substantially no trialkoxysilane present.

32. A rubber compound as defined in claim 21, further comprising a catalyst for an alkoxysilane-silica reaction.

33. A rubber compound as defined in claim 32, wherein the catalyst for the alkoxysilane-silica reaction is selected from the group consisting of a strong organic base having a $pK_a$ in aqueous media of greater than about 10, a strong inorganic base, an alkyl tin catalyst, a zirconium catalyst, a titanium catalyst, and combinations thereof.

34. A rubber compound as defined in claim 33, wherein the strong organic base catalyst is selected from the group consisting of strong alkali metal alkoxides; guanidines; hindered amines; tertiary amines; quaternary ammonium bases; bis-aminoethers; and nitrogen-containing heterocycles having from 5 to 7 ring members, and combinations thereof.

35. A rubber compound as defined in claim 34, wherein the nitrogen-containing heterocycle comprises a substituted or unsubstituted imidazole.

36. A rubber compound as defined in claim 35, wherein the substituted or unsubstituted imidazole is selected from the group consisting of imidazole, 4-ethylamino imidazole, 2-mercapto-1-methyl imidazole, 1-methyl imidazole, 2,4,5-triphenyl imidazole, 2-methyl imidazole, 2-ethyl-4-methyl imidazole, 2-heptadecyl imidazole, and combinations thereof.

37. A rubber compound as defined in claim 34, wherein the guanidine is selected from the group consisting of triphenylguanidine, diphenylguanidine, di-o-tolylguanidine, N,N,N',N'-tetramethylguanidine, and combinations thereof.

38. A rubber compound as defined in claim 37, wherein the guanidine comprises diphenylguanidine.

39. A rubber compound as defined in claim 33, wherein the strong organic base is present in an amount of 0.003 phr to about 8 phr.

40. A rubber compound as defined in claim 33, wherein the alkyl tin catalyst is selected from the group consisting of butyl tin tris(2-ethylhexanoate), bis(2-ethyl-hexanoate) tin, butyl tin chloride dihydroxide, butyl tin hydroxide oxide hydrate, dibutyl tin dilaurate, dibutyl tin dimaleate, dibutyl tin oxide, and combinations thereof.

41. A rubber compound as defined in claim 33, wherein the alkyl tin catalyst comprises bis(2-ethyl-hexanoate) tin.

42. A rubber compound as defined in claim 33, wherein the alkyl tin catalyst is present in an amount of about 0.01% to about 5% by weight, based on the weight of the silica.

43. A rubber compound as defined in claim 33, wherein the zirconium catalyst is selected from the group consisting of zirconium 2-ethylhexanoate, zirconium tetrakis-(2-ethylhexanoate), tetraoctyl zirconate, zirconium n-butoxide, zirconium t-butoxide, zirconium di-n-butoxide (bis-2,4-pentanedionate), zirconium diisopropoxide bis(2,2,6,6-tetramethyl-3,5-heptanedionate), zirconium ethoxide, zirconium 2-ethylhexoxide, zirconium 3,5-heptanedionate, zirconium isopropoxide, zirconium 2-methyl-2-butoxide, zirconium 2,4-pentanedionate, zirconium n-propoxide, and combinations thereof.

44. A rubber compound as defined in claim 33, wherein the zirconium catalyst comprises zirconium 2-ethylhexanoate.

45. A rubber compound as defined in claim 33, wherein the zirconium catalyst is present in an amount of about 0.01% to about 5% by weight, based on the weight of the silica.

46. A rubber compound as defined in claim 33, wherein the titanium catalyst is selected from the group consisting of titanium trimethylsiloxide, titanium (isopropoxide)$_2$(2,4-pentandionate)$_2$, titanium (butoxide)$_2$(2,4-pentandionate)$_2$, titanium (isopropoxide)$_2$(ethyl-acetoacetate)$_2$, and combinations thereof.

47. A rubber compound as defined in claim 21, wherein at least one of the $R^1$, $R^2$ and $R^3$ groups of the alkoxy-modified silsesquioxane is a group that binds to the elastomer.

48. A rubber compound as defined in claim 21, wherein the at least one of the $R^1$, $R^2$ and $R^3$ groups of the alkoxy-modified silsesquioxane is selected from the group consisting of a mercaptoalkyl group, a blocked mercaptoalkyl group, and an organo group containing a chain of about 2 to about 8 sulfur atoms.

49. A rubber compound as defined in claim 21, wherein the one or more alkoxy-modified silsesquioxanes is an alkyl alkoxy-modified silsesquioxane.

50. A rubber compound as defined in claim 21, wherein the alkoxy-modified silsesquioxane is selected from the group consisting of octyl alkoxy-modified silsesquioxanes, phenyl alkoxy-modified silsesquioxanes, 3-chloropropyl alkoxy-modified silsesquioxanes, 3-mercaptopropyl alkoxy-modified silsesquioxanes, 2-thioacylpropyl alkoxy-modified silsesquioxanes, and mixtures thereof.

51. A rubber compound as defined in claim 21, wherein the rubber compound further comprises a non-alkoxysilane silica shielding agent.

52. A rubber compound as defined in claim 51, wherein the non-alkoxysilane silica shielding agent is selected from the group consisting of glycols, fatty acid esters of hydrogenated or non-hydrogenated $C_5$ or $C_6$ sugars, polyoxyethylene derivatives of fatty acid esters of hydrogenated or non-hydrogenated $C_5$ or $C_6$ sugars, and mixtures thereof.

53. A pneumatic tire including at least one component comprising a vulcanized rubber that comprises a vulcanized rubber compound comprising (a) an elastomer;
(b) a reinforcing filler comprising silica or a mixture thereof with carbon black;
(c) a silica dispersing aid comprising an alkoxy-modified silsesquioxane that comprises one or more compounds selected from the group consisting of alkoxy-modified silsesquioxanes having the formula

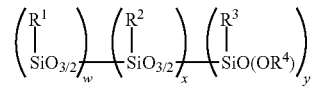

and mixtures thereof, wherein w, x and y represent mole fractions, y does not equal zero, either w or x but not both can be zero, and w+x+y=1.00, wherein $R^1$, $R^2$ and $R^3$ are selected from the group consisting of (i) H or an alkyl groups having one to about 20 carbon atoms, (ii) cycloalkyl groups having 3 to about 20 carbon atoms, (iii) alkylaryl groups having 7 to about 20 carbon atoms, and (iv) $R^5X$, wherein X is selected from the group consisting of Cl, Br, SH, $S_aR^6$, $NR^6{}_2$, $OR^6$, $CO_2H$, $CO_2R^6$, $SCOR^6$, OH, olefins, epoxides, amino groups, vinyl groups, acrylates and methacrylates, wherein a=1 to about 8, $R^5$ is selected from the group consisting of alkylene groups having one to about 20 carbon atoms, cycloalkylene groups having 3 to about 20 carbon atoms, and $R^4$ and $R^6$ are selected from the group consisting of alkyl groups having one to about 5 carbon atoms, cycloalkyl having 3 to about 20 carbon atoms, and alkylaryl groups having 7 to about 20 carbon atom, wherein the alkoxy-modified silsesquioxanes consist essentially of a mixture of alkoxy-modified silsesquioxanes having an open structure with a reactive alkoxysilyl group, and essentially free of closed caged polyhedral organosilsesquioxanes, and wherein the mixture of alkoxy-modified silsesquioxanes liberates about 0.05% to about 10% by weight alcohol when treated by substantially total acid hydrolysis; and (d) a cure agent.

54. A pneumatic tire as defined in claim 53, wherein the silica is present in an amount of about 15 phr to about 120 phr.

55. The pneumatic tire of claim 53, wherein the alkoxy-modified silsesquioxane is present in an amount of about 0.1% to about 20% by weight based on the silica.

56. The pneumatic tire of claim 53, wherein the elastomer is selected from the group consisting of homopolymers of a conjugated diene monomer, and copolymers and terpolymers of the conjugated diene monomers with monovinyl aromatic monomers and trienes.

57. The pneumatic tire of claim 53, wherein the elastomer is selected from the group consisting of styrene/butadiene copolymer, polyisoprene, polybutadiene, butadiene/isoprene copolymer, butadiene/isoprene/styrene terpolymers, isoprene/styrene copolymer, natural rubber, butyl rubber, ethylene-propylene-diene rubber and combinations thereof.

58. The pneumatic tire of claim 53, wherein the vulcanized rubber is sulfur-vulcanized.

59. A pneumatic tire as defined in claim 53, further comprising a sulfur containing coupling agent.

60. A pneumatic tire as defined in claim 59, wherein the sulfur containing coupling agent is present in an amount of about 0.05% to about 3% based on the amount of silica present.

61. A pneumatic tire as defined in claim 59, wherein the sulfur containing coupling agent is selected from the group consisting of mercaptoalkyltrialkoxy silanes, blocked mercaptoalkyltrialkoxy silanes, mercaptoalkylsilanes bound to silica, blocked mercaptoalkylsilanes bound to silica, bis(trialkoxysilylorgano) tetrasulfides or disulfides, and mixtures thereof.

62. A pneumatic tire as defined in claim 59, wherein the sulfur containing coupling agent is a mercaptosilane fixed to silica with substantially no trialkoxysilane present.

63. A pneumatic tire as defined in claim 53, further comprising a catalyst for an alkoxysilane-silica reaction.

64. A pneumatic tire as defined in claim 63, wherein the catalyst for the alkoxysilane-silica reaction is selected from the group consisting of a strong organic base having a $pK_a$ in aqueous media of greater than about 10, a strong inorganic base, an alkyl tin catalyst, a zirconium catalyst, a titanium catalyst, and combinations thereof.

65. A pneumatic tire as defined in claim 64, wherein the strong organic base catalyst is selected from the group consisting of strong alkali metal alkoxides; guanidines; hindered amines; tertiary amines; quaternary ammonium bases; bis-aminoethers; and nitrogen-containing heterocycles having from 5 to 7 ring members, and combinations thereof.

66. A pneumatic tire as defined in claim 64, wherein the alkyl tin catalyst is selected from the group consisting of butyl tin tris(2-ethylhexanoate), bis(2-ethyl-hexanoate) tin, butyl tin chloride dihydroxide, butyl tin hydroxide oxide hydrate, dibutyl tin dilaurate, dibutyl tin dimaleate, dibutyl tin oxide, and combinations thereof.

67. A pneumatic tire as defined in claim 64, wherein the zirconium catalyst is selected from the group consisting of zirconium 2-ethylhexanoate, zirconium tetrakis-(2-ethylhexanoate), tetraoctyl zirconate, zirconium n-butoxide, zirconium t-butoxide, zirconium di-n-butoxide (bis-2,4-pentanedionate), zirconium diisopropoxide bis(2,2,6,6-tetramethyl-3,5-heptanedionate), zirconium ethoxide, zirconium 2-ethylhexoxide, zirconium 3,5-heptanedionate, zirconium isopropoxide, zirconium 2-methyl-2-butoxide, zirconium 2,4-pentanedionate, zirconium n-propoxide, and combinations thereof.

68. A pneumatic tire as defined in claim 64, wherein the titanium catalyst is selected from the group consisting of titanium trimethylsiloxide, titanium (isopropoxide)$_2$(2,4-pentandionate)$_2$, titanium (butoxide)$_2$(2,4-pentandionate)$_2$, titanium (isopropoxide)$_2$(ethyl-acetoacetate)$_2$, and combinations thereof.

69. The pneumatic tire of claim 53, wherein the tire component is selected from the group consisting of treads, sub-treads, sidewalls, body ply skims, bead fillers, apex, chafer, sidewall insert, wirecoat, inner liner, and combinations thereof.

70. The pneumatic tire of claim 69, wherein the tire component is a tread.

71. A method for producing a vulcanizable rubber composition with low VOC release during compounding comprising:

(a) forming a mixture by mixing together at a mixing temperature:

(i) an elastomer;

(ii) a reinforcing filler comprising silica or a mixture thereof with carbon black; and (iii) a silica dispersing aid comprising an alkoxy-modified silsesquioxane that comprises one or more compounds selected from the group consisting of alkoxy-modified silsesquioxanes having the formula

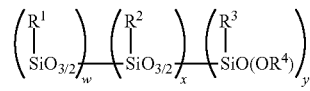

and mixtures thereof, wherein w, x and y represent mole fractions, y does not equal zero, either w or x but not both can be zero, and w+x+y=1.00, wherein $R^1$, $R^2$ and $R^3$ are selected from the group consisting of (i) H or an alkyl groups having one to about 20 carbon atoms, (ii) cycloalkyl groups having 3 to about 20 carbon atoms, (iii) alkylaryl groups having 7 to about 20 carbon atoms, and (iv) $R^5X$, wherein X is selected from the group consisting of Cl, Br, SH, $S_aR^6$, $NR^6{}_2$, $OR^6$, $CO_2H$, $CO_2R^6$, $SCOR^6$, OH, olefins, epoxides, amino groups, vinyl groups, acrylates and methacrylates, wherein a=1 to about 8, $R^5$ is selected from the group consisting of alkylene groups having one to about 20 carbon atoms, cycloalkylene groups having 3 to about 20 carbon atoms, and $R^4$ and $R^6$ are selected from the group consisting of alkyl groups having one to about 5 carbon atoms, cycloalkyl groups having 3 to about 20 carbon atoms, and alkylaryl groups having 7 to about 20 carbon atoms;

(b) cooling the mixture to a temperature below the mixing temperature; and (c) mixing a vulcanizing agent into the mixture at a temperature lower than a vulcanization temperature, wherein the alkoxy-modified silsesquioxanes consist essentially of a mixture of alkoxy-modified silsesquioxanes having an open structure with a reactive alkoxysilyl group, and essentially free of closed caged polyhedral organosilsesquioxanes, and wherein the mixture of alkoxy-modified silsesquioxanes liberates about 0.05% to about 10% by weight alcohol when treated by substantially total acid hydrolysis.

72. A method as defined in claim 71, wherein the mixing temperature is about 130° C. to about 200° C.

73. A method as defined in claim 71, wherein the mixing temperature is about 145° C. to about 190° C.

74. A method as defined in claim 71, wherein the mixing temperature is about 155° C. to about 180° C.

75. A method as defined in claim 71, wherein the silica is present in an amount of about 15 phr to about 120 phr.

76. A method as defined in claim 71, wherein the alkoxy-modified silsesquioxane is present in an amount of about 0.1% to about 20% by weight based on the silica.

77. A method as defined in claim 71, wherein the mixture of alkoxy-modified silsesquioxanes liberates about 0.1% to about 8% by weight alcohol when treated by substantially total acid hydrolysis.

78. A method as defined in claim 71, wherein the mixture of alkoxy-modified silsesquioxanes liberates about 1% to about 6% by weight alcohol when treated by substantially total acid hydrolysis.

79. A method as defined in claim 71, wherein an amount of alcohol released as VOC during compounding and further processing is zero to about 0.1% by weight of the rubber compound.

80. A method as defined in claim 71, wherein an amount of alcohol released as VOC during compounding and further processing is zero to about 0.05% by weight of the rubber compound.

81. A method as defined in claim 71, wherein the elastomer is selected from the group consisting of homopolymers of a conjugated diene monomer, and copolymers and terpolymers of the conjugated diene monomers with monovinyl aromatic monomers and trienes.

82. A method as defined in claim 71, wherein the elastomer is selected from the group consisting of styrene/butadiene copolymer, polyisoprene, polybutadiene, butadiene/isoprene copolymer, butadiene/isoprene/styrene terpolymers, isoprene/styrene copolymer, natural rubber, butyl rubber, ethylene-propylene-diene rubber and combinations thereof.

83. A method as defined in claim 71, further comprising a sulfur containing coupling agent.

84. A method as defined in claim 83, wherein the sulfur containing coupling agent is present in an amount of about 0.05% to about 3% based on the amount of silica present.

85. A method as defined in claim 83, wherein the sulfur containing coupling agent is selected from the group consisting of mercaptoalkyltrialkoxy silanes, blocked mercaptoalkyltrialkoxy silanes, mercaptoalkylsilanes bound to silica, blocked mercaptoalkylsilanes bound to silica, bis(trialkoxysilylorgano) tetrasulfides or disulfides, and mixtures thereof.

86. A method as defined in claim 83, wherein the sulfur containing coupling agent is a mercaptosilane fixed to silica with substantially no trialkoxysilane present.

87. A method as defined in claim 71, further comprising a catalyst for an alkoxysilane-silica reaction.

88. A method as defined in claim 87, wherein the catalyst for the alkoxysilane-silica reaction is selected from the group consisting of a strong organic base having a $pK_a$ in aqueous media of greater than about 10, a strong inorganic base, an alkyl tin catalyst, a zirconium catalyst, a titanium catalyst, and combinations thereof.

89. A method as defined in claim 88, wherein the strong organic base catalyst is selected from the group consisting of strong alkali metal alkoxides; guanidines; hindered amines; tertiary amines; quaternary ammonium bases; bis-aminoethers; and nitrogen-containing heterocycles having from 5 to 7 ring members, and combinations thereof.

90. A method as defined in claim 88, wherein the alkyl tin catalyst is selected from the group consisting of butyl tin tris(2-ethylhexanoate), bis(2-ethyl-hexanoate) tin, butyl tin chloride dihydroxide, butyl tin hydroxide oxide hydrate, dibutyl tin dilaurate, dibutyl tin dimaleate, dibutyl tin oxide, and combinations thereof.

91. A method as defined in claim 88, wherein the zirconium catalyst is selected from the group consisting of zirconium 2-ethylhexanoate, zirconium tetrakis-(2-ethylhexanoate), tetraoctyl zirconate, zirconium n-butoxide, zirconium t-butoxide, zirconium di-n-butoxide (bis-2,4-pentanedionate), zirconium diisopropoxide bis(2,2,6,6-tetramethyl-3,5-heptanedionate), zirconium ethoxide, zirconium 2-ethylhexoxide, zirconium 3,5-heptanedionate, zirconium isopropoxide, zirconium 2-methyl-2-butoxide, zirconium 2,4-pentanedionate, zirconium n-propoxide, and combinations thereof.

92. A method as defined in claim 88, wherein the titanium catalyst is selected from the group consisting of titanium trimethylsiloxide, titanium (isopropoxide)$_2$(2,4-pentandionate)$_2$, titanium (butoxide)$_2$(2,4-pentandionate)$_2$, titanium (isopropoxide)$_2$(ethyl-acetoacetate)$_2$, and combinations thereof.

* * * * *